US007112576B1

(12) United States Patent
Hubel

(10) Patent No.: US 7,112,576 B1
(45) Date of Patent: Sep. 26, 2006

(54) COMPOSITIONS AND METHODS FOR CRYOPRESERVATION OF PERIPHERAL BLOOD LYMPHOCYTES

(75) Inventor: Allison Hubel, St. Paul, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 701 days.

(21) Appl. No.: 09/458,862

(22) Filed: Dec. 10, 1999

(51) Int. Cl.
*A61K 31/70* (2006.01)
(52) U.S. Cl. ........................................... 514/54
(58) Field of Classification Search .................. 514/54
See application file for complete search history.

(56) References Cited

U.S. PATENT DOCUMENTS

| | | | | |
|---|---|---|---|---|
| 4,386,069 | A | 5/1983 | Estep | 424/101 |
| 4,415,556 | A | 11/1983 | Bretschneider | 424/153 |
| 4,639,373 | A | 1/1987 | Babior | 424/101 |
| 4,663,289 | A | 5/1987 | Veech | 435/240 |
| 4,961,928 | A | 10/1990 | Holme et al. | 424/533 |
| 5,043,261 | A | 8/1991 | Goodrich et al. | 435/2 |
| 5,045,446 | A | 9/1991 | Goodrich, Jr. et al. | 435/2 |
| 5,061,620 | A | 10/1991 | Tsukamoto et al. | 435/7.21 |
| 5,116,969 | A | 5/1992 | Adams et al. | 536/128 |
| 5,178,884 | A | 1/1993 | Goodrich, Jr. et al. | 424/533 |
| 5,364,756 | A | 11/1994 | Livesey et al. | 435/2 |
| 5,422,261 | A | 6/1995 | Lee et al. | 435/219 |
| 5,425,951 | A | 6/1995 | Goodrich, Jr. et al. | 414/520 |
| 5,478,576 | A | 12/1995 | Jung et al. | 424/488 |
| 5,580,714 | A | 12/1996 | Polovina | 435/2 |
| 5,756,098 | A | 5/1998 | Price et al. | 424/195.1 |
| 5,770,700 | A | 6/1998 | Webb et al. | 530/383 |
| 5,897,987 | A | 4/1999 | Oliver et al. | 435/1.3 |
| 5,955,257 | A | 9/1999 | Burger et al. | 435/2 |
| 6,277,557 | B1 | 8/2001 | Burger et al. | 435/2 |

FOREIGN PATENT DOCUMENTS

| | | |
|---|---|---|
| DE | 19758073 | 7/1999 |
| EP | 0356257 B1 | 3/1995 |
| WO | WO-91/18504 | 12/1991 |
| WO | WO-92/08347 | 5/1992 |
| WO | WO-92/14360 | 9/1992 |
| WO | WO-93/07745 | 4/1993 |
| WO | WO-95/10291 | 4/1995 |
| WO | 97/35472 | 10/1997 |

OTHER PUBLICATIONS

*Cellsep Lymphocytes 50 ml Protocol*, Larex, Inc., St. Paul, MN, 4 p., (Aug. 5, 1996).
*Larex Material Safety Data Sheet*, Larex, Inc., St. Paul, MN, 3 p., (Aug. 5, 1996).
Areman, et al., "Processing and Storage of Human Bone Marrow; A Survey of Current Practices in North America", *Bone Marrow Transplant*, 6 (3), pp. 203-209, (1990).
Areman, E.M., et al., "Bulk cryopreservation of lymphocytes in glycerol", *Transfusion*, 28 (2), pp. 151-156, (1988).

Gee, A.P., "Hematopoietic Stem Cell Engineering—The Magic Bullet of the Next Millenium?", HTD-vol. 355/BED-vol. 37, *Advances in Heat and Mass Transfer in Biotechnology*, ASME 1997, pp. 95-96, (1997).
Hubel, A., et al., "Cryobiophysical Characteristics of Genetically Modified Hematopoietic Progenitor Cells", *Cryobiology*, 38 (2), pp. 140-153, (Mar. 1999).
Hubel, A., et al., "Crypreservation of Cultured Blood Cells for Use in Gene Therapy and Immunotherapy", HTD-vol. 355/BED-vol. 37, *Advances in Heat and Mass Transfer in Biotechnology*, ASME 1997, pp. 97-98, (1997).
Luo, K., et al., "Effect of Dimethylsulfoxide and Hydroxyethyl Starch in the Preservation of Fractionated Human Marrow Cells", *Cryobiology*, 31, pp. 349-354, (1994).
Nei, T., "Mechanism of Freezing Injury to Erythrocytes: Effects of Initial Cell Concentration on the Post-thaw Hemolysis", *Cryobiology*, 18, pp. 229-237, (1981).
Pegg, D.E., "Perfusion of Rabit Kidneys with Cryoprotective Agents", *Cryobiology*, 9, pp. 411-419, (1972).
Stroneck, D.F., et al., "Retroviral transduction and expansion of peripheral blood lymphocytes for the treatment of mucopolysaccharidosis type II, Hunter's syndrome", *Transfusion*, 39(4), Abstract, http://www.ncbi.nlm.nih.gov, (1999).
Zambelli, A., et al., "Clinical toxicity of cryopreserved circulating progenitor cells infusion", *Anticancer Res.*, 18(6B), Abstract, http://www.ncbi.nlm.nih.gov, (1998).
*Standards for Hematopoietic Progenitor Cell Collection, Processing & Transplantation*, First Edition, Foundation for the Accreditation of Hematopoietic Cell Therapy,(1996),1-58.
Ager, S..,et al. ,"The use of non-cryopreserved peripheral blood progenitor cells in autologous transplantation", *Bone Marrow Transplantation*, 16, (1995),633-34.
Ahmed, Tauseef.,et al. ,"Marrow Storage Techniques: a Clinical Comparison of Refrigeration versus Cyropreservation", *Acta Haematol*, (1991),173-178.
Ahmed, Tauseef.,et al. ,"Refrigeration Storage of Bone Marrow", *Bone Marrow and Stem Cell Processing: A Manual of Current Techniques*, 332-334.
Anderlini,et al. ,"Clinical Toxicity and Laboratory Effects of Granulocyte-Colony-Stimulating Factor (Filgrastim) Mobilization and Blood Stem Cell Apheresis from Normal Donors, and Analysis of Charges for the Procedures", *Transfusion*, 36, (Jul. 1996),590-595.
Areman, E.M. ,et al. , *Bone Marrow and Stem Cell Processing: A Manual of Current Techniques*, F.A. Davis Company, Philadelphia, PA,(1992),xvii-xxx.
Areman, Ellen.,"ISHAGE: The Next Step", *Journal of Hematotherapy*, 6, (Oct. 1997),437-438.
Areman, E..M. ,et al. ,"Use of a Licensed Eletroylyte Solution as an Alternative to Tissue Culture Medium for Bone Marrow Collection", *Transfusion 33*, (1993),562-566.

(Continued)

Primary Examiner—Elli Peselev
(74) *Attorney, Agent, or Firm*—Schwegman, Lundberg, Woessner & Kluth, P.A.

(57) ABSTRACT

A composition and method for cryopreserving cells in a non-toxic medium is described. The composition and method provide cells for cell therapy and other in vivo applications.

52 Claims, 3 Drawing Sheets

OTHER PUBLICATIONS

Areman, et al., "Use of Licensed Electrolyte Solutions and Anticoagulant Citrate Dextrose for Bone Marrow Collection", *Advances in Bone Marrow Purging and Processing*, (1992),353-359.

Barnes, David.H., et al., "The Radiation Recovery Factor: Preservation by the Polge-Smith-Parkes Technique", *Journal of National Cancer Institute*, vol. 15, No. 4, (Feb. 1955),901-905.

Batinic, D.., et al., "Relationship between differing volumes of bone marrow aspirates and their cellular composition", *Bone Marrow Transplantation 6*, (1990),103-107.

Beaujean, Francoise., et al., "Characteristics of Peripheral Blood Progenitor Cells Frozen After 24 hours of liquid storage", *Journal of Hematotheraphy*, (1996),681-686.

Bezwoda, W..R., et al., "Non-cryopreserved, limited No. (1 or 2) peripheral blood progenitor cell (PBPC) collections following GCSF administration provide adequate hematologic support for high dose chemotherapy", *Hematological Oncology*, 12, (1994),101-110.

Burger, S..R., et al., "Development of an infusible-grade hematopoietic cell storage solution", From the Dept. of Laboratory Medicine and Pathology, The University of Minnesota Medical School, Minneapolis, MN, (1998),1-49.

Burnett, A..K., et al., "Haematological reconstitution following high dose and supralethal chemo-radiotheraphy using stored, non-cryopreserved autologous bone marrow", *British Journal of Haematology*, 54, (1983),309-316.

Carella, Angelo.M., et al., "Massive Chemotherapy with non-Frozen Autologous Bone Marrow Transplantation in 13 Cases of Refractory Hodgkin's Disease", *Eur J Cancer Clin Oncol*, 21, (1985),607-813.

Carey, P.J., et al., "Autologous Bone Marrow Transplantation for High-Grade Lymphoid Malignancy Using Melphalan/Irradiation Conditioning Without Marrow Purging or Cryopreservation", *Blood*, 77, (Apr. 1, 1991),1593-1598.

D'Amico, Elbio.A., et al., "Bone Marrow harvesting from hemophilia A donor" *The Lancey*, (Jan. 23, 1993),254.

Delforge, Alian., et al., "Granuloucyte-macrophage progenitor cell preservation at 4 degree C", *British Journal of Haematology*, (1983),49-54.

Ende, Norman., et al., "Potential effectiveness of stored cord blood (non-frozen) for emergency use", *The Journal of Emergency Medicine*, 14, (1996),673-677.

Fahy, Gregory.M., et al., "Cryoprotectant Toxicity and Cryoprotectant Toxicity Reduction: In Search of molecular Mechanisms", *Cryobiology* 27, (1990),247-268.

Gutensohn, K.., et al., "Storage of Peripheral Blood Stem Cell Samples Alters Flow Cytometric CD34+Results", *Beitr Infusionether Transfusionsmed.*, (1996),170-174.

Hechler, G.., et al., "Storage of noncryopreserved peripheral blood stem cells for transplantation", *Ann Hematol*, 72, (1996),303-306.

Holdreinet, J..V., et al., "A Method of Quantification of Peripheral Blood Admixture in Bone Marrow Aspirates", *Exp. Hermat.*, Jan. 1980, vol. 8, No. 1, (Jan. 1980),103-107.

Issaragrisil, S.., et al., "Preservation of Haemopoietic Progenitor Cells", *Transplantation*, 36, (1983),341-3.

Janssen, W.E., et al., "Shipping of Freshly Harvested Bone Marrow", *Bone Marrow and Stem Cell Processing: A Manual of Current Techniques*, (1992),445-448.

Jestice, H..K., et al., "Liquid storage of peripheral blood progenitor cells for transplantation", *Bone Marrow Transplantation*, 14, (1994),991-994.

Jones, N.., et al., "High-dose Melphalan Followed by Autograft Employing Non-cryopreserved Peripheral Blood Progenitor Cells in Children", *European Journal of Cancer*, 32, (1996),1938-1942.

Killian, Donna., et al., "A cost-effective and Food and Drug Administration-approved alternative to tissue culture media in cryopreservation", *Transfusion*, 36, (1996),476.

Kohsaki, et al. "Non-Frozen Preservation of Committed Hematopoietic Stem Cells from Normal Human Bone Marrow", *Stem Cells*, 1, (1981),111-123.

Lasky, et al., "Liquid Storage of Unseparated Human Bone Marrow : Evaluation of Hematopoietic Progenitors by Clonal Assay", *Transfusion*, 26 vol. 4, (1986),331-334.

Lennard, A..L., et al., "Peripheral blood stem-cell transplantation versus non-cryopreserved autologous bone-marrow transplantation", *The Lancey*, (Jan. 23, 1993),254.

Luo, K., et al., "Dimethylsulfoxide and Hydroxyethyl Starch in the Preservation of Fractionated Human Marrow Cells", *Cryobiology* vol. 31, No. 4, (1994),349-354.

Mangalik, et al., "Liquid Storage of Bone Marrow", *Experimental Hematology*, 7, (1979),76-94.

Millar, John.L., et al., "The Viability of Marrow Stored at 4 degree C", *Autologous Bone Marrow Transplantation and Solid Tumors*, edited by J.G. McVie, et al., (1984),9-12.

Murea, Simona., et al., "Granulocytes Harvested Following G-CSF-Enhanced Leukocyte Recovery Retain Their Functional Capacity During In Vitro Culture for 72 Hours", *Journal of Hematotheraphy*, 5, (1996),351-357.

Nei, T.., "Mechanism of Freezing Injury to Erythrocytes: Effects of Initial Cell Concentration on the Post-thaw Hemolysis", *Cryobiology*, 18, (1981),pp. 229-237.

Niskanen, "Preservation of Human Granulopoietic Precursors Following Storage in the Nonfrozen State", *Transplantation*, 36, (1983),341-343.

Pegg, D..E., "Freezing of Bone Marrow For Clinical Use", *Cryobiology*, 1, (1964),64-71.

Pettengell, R.., et al., "Viability of haemopoietic progenitors from whole bolld, bone marrow and leukapheresis product: effects of storage media, temperature and time", *Bone Marrow Transplantation*, 14, (1994),703-709.

Phillips, G.., et al., "American Socierty for Blood and Marrow Transplantation Guidelines for Clinical Centers", *Biology of Blood and Marrow Transplantation*, 1, (1995),54-55.

Preti, R..A., et al., "Clinical and laboratory comparison study of refrigerated and cryopreserved bone marrow for transplantation", *Bone Marrow Transplantation*, 13, (1994),253-260.

Raju, G..M., et al., "Storage of Haemopoietic Stem Cells for Autologous Bone Marrow Transplantation", *National Medical J. of India*, 8 (5), (1995),216-221.

Robinson, W.A., "Autologous Non Frozen Bone Marrow Transplantation after Intensive Chemotherapy: A Pilot Study", *Acta Haemat.*, 66, (1981),145-15.

Rossi, et al., "Transfusion in Transition", *In: Principles of Transfusion Medicine*, Williams and Wilkins Publishers; Baltimore, Maryland, (1990),1-11.

Ruiz-Arguelles, Guillermo.J., et al., "Filgrastim-mobilized peripheral-blood stem cells can be stored at 4 degrees and used in autografts to rescue high-dose chemotherapy", *American Journal of Hematology*, 48, (1995),100-103.

Sputtek, et al., "Chapter V. Stem Cells", *In: Clinical Applications of Cryobiology*, B.J. Fuller, et al., (Eds.), CRC Press, (1991),127-147.

Stroncek, et al., "Treatment of Normal Individuals with Granulocyte-Colony-Stimulating Factor: Donor Experiences and the Effects on Peripheral Blood CD34+Cell Counts and on the Collection of Peripheral Blood Stem Cells", *Transfusion*, 36, (Jul. 1996),601-610.

Surgrue, M.., et al., "The effect of overnight storage of leukapheresis stem cell products (LSCP) on cell viability and cost", *Journal of Hematotheraphy*, 7, (1998),pp. 431-436.

Tajima, Tomoo., "The Effects of Non-cryopreservation on Clony Formation of Committed Progenitor Cells of Bone Marrow", *Tokai J. Exp. Clin. Med.*, 13 (1), (1988),15-22.

Takahashi, Mashuhiro., et al., "Effects of Marrow Storage at 4 degree C on the Subsequent Generation of Long-term Marrow Cultures", *Experimental Hermatology*, 13, (1985),691-695.

Thomas, et al., "Technique for Human Marrow Grafting", *BLOOD The Journal of Hematology*, 36, (Oct. 1970),507-515.

Wells, et al., "Preservation of Granulopoietic Precursors in Nonfrozen, Stored Human Bone Marrow", *Transplantation*, 22, (1976),568-571.

COMPOSITIONS AND METHODS FOR CRYOPRESERVATION OF PERIPHERAL BLOOD LYMPHOCYTES

STATEMENT OF GOVERNMENT SUPPORT

The invention was made at least in part with a grant from the Government of the United States of America (grant P01-HD32652 from the National Institutes of Health). The Government may have certain rights to the invention.

BACKGROUND OF THE INVENTION

Lymphocytes have been studied extensively for the treatment of solid tumors and viral infections, as an adjuvant to bone marrow transplantation, and for the treatment of genetic diseases. For example, early immunotherapy studies for the treatment of melanoma and renal cell carcinoma focused on lymphokine-activated killer (LAK) cells or tumor infiltrating lymphocytes (TILs) (Rosenberg, 1985; Rosenberg, 1987; Rosenberg, 1988), cytotoxic T lymphocytes have been used for the treatment of AIDS (Koenig, 1995; Torpey, 1993; Trickett, 1998), and donor lymphocyte infusions are used after allogeneic bone marrow transplant to enhance graft-versus-leukemia effect and to reduce the potential for relapse (Kolb, 1997). Furthermore, genetically modified peripheral blood lymphocytes (PBLs) have been used in clinical trials for the treatment of severe combined immune deficiency caused by adenosine deaminase (ADA) deficiency (Blaese, 1995), and a variety of other lymphocyte-based therapies have been proposed, including transducing lymphocytes with the herpes simplex virus (HSV) thymidine kinase (TK) suicide gene for allogeneic bone marrow transplantation (Bonini, 1997) and the introduction of cytotoxic T lymphocytes (CTLs) that recognize specific melanomal antigens (Kawakami, 1998).

Cryopreservation of cells that have been expanded and manipulated ex vivo is important for the clinical application of cell-based therapies. Cryopreservation facilitates pooling of cells to reach a therapeutic dose, and facilitates safety testing of both the cell product and any agents, such as recombinant viral vectors or liposomal delivery vehicles, used to genetically modify the cells. Furthermore, as the genetic modification and/or expansion of cells for therapeutic use may require days to weeks for completion of the ex vivo culture protocol, cryopreservation facilitates the coordination of cellular therapy with donor care.

In the method most commonly used for the cryopreservation of bone marrow, peripheral blood lymphocytes (PBLs) are resuspended in a cryopreservation medium containing 10% dimethylsulfoxide (DMSO), autologous plasma and Hank's balanced salt solution (Rowley, 1994; Trickett, 1998) and cooled at 1° C./minute. A second method involves freezing lymphocytes in a 20% glycerol solution supplemented with autologous serum (Areman, 1988), resulting in increased cell viability over the standard DMSO protocol. Glycerol-based cryopreservation solutions have also been reported for hematopoietic progenitor cells (U.S. Pat. No. 5,759,764), however, glycerol has lower permeability, which increases the chance for cell loss from osmotic stresses. Although Oliver et al. (WO 97/35472) relate to a combination of arabinogalactan and cell culture media as useful as a cryopreservation medium, the data was obtained from cell lines, not primary cells.

DMSO cryopreservation involves the risk of DMSO-associated toxicity, particularly where cell transfer therapy is involved. For example, Zambelli et al. (1998) evaluated the infusion-related toxicity of transplanted cryopreserved cells and determined that the amount of DMSO present in the graft is related to the grade of toxicity. Davis et al. (1990) found that almost all patients who received cryopreserved autologous cell grafts exhibited dyspnea (83%), decreased heart rates (98%), and transient hypertension (96%), which were attributed to the infusion of DMSO. Oliguric renal failure and second degree heart block were less frequently observed. Similar results were observed in a study by Stroncek et al. (1991), who found that infusion-related reactions, principally nausea and chills, were associated with transplantation of cryopreserved bone marrow. Moreover, in pediatric patients, higher levels of nausea, vomiting, cardiac arrhythmia and hypotension are noted following transplant of cryopreserved bone marrow (Okamoto, 1993). Since most lymphocyte therapies require the infusion of multiple doses of cells on a regular basis, the toxic effects of DMSO can be cumulative.

The development of appropriate solutions is not the only issue in the development of cryopreservation protocols for lymphocytes which are used therapeutically. Recent studies indicate that in vitro culture influences the freezing response of cells. For example, studies of in vitro cultured hematopoietic progenitor cells and lymphocytes indicates that water transport and intracellular ice formation characteristics of the cells is influenced by in vitro culture (Hubel, 1999). Specifically, subzero water transport characteristics of the cells and postthaw viability were influenced by time in culture.

Thus, what is needed is a cryopreservation composition that is non-toxic and useful for achieving the desired viability rates for cryopreservation of cells for cellular therapy.

SUMMARY OF THE INVENTION

The present invention provides a cryopreservation medium for hematopoietic cells which incorporates a balanced electrolyte solution with at least one cryoprotective agent that is arabinogalactan (AG), or a biological or functional equivalent thereof. The cryoprotective agent(s) is present in the cryopreservation medium in an amount effective to promote a high survival rate for the cryopreserved cells. Preferably, the medium does not comprise DMSO or serum, although purified protein, e.g., human serum albumin, may, optionally, be included. In one embodiment of the invention, the cryopreservation medium does not comprise protein. In yet another embodiment of the cryopreservation medium of the invention, the medium comprises glycerol, e.g., about 0.5% to about 20%, preferably about 0.75% to about 10%, more preferably about 1% to about 6%, and even more preferably about 1% to about 5%, volume/volume (v/v).

As defined herein "ultrarefined arabinogalactan" refers to arabinogalactan, isolated from a plant source such as from trees of the genus *Larix*, preferably with a purity greater than 95%. The molecular weight of the arabinogalactan in one embodiment ranges from about 6,000 to 2,500,000, preferably from about 10,000 to about 50,000, and more preferably from about 15,000 to about 25,000. Preferred amounts of arabinogalactan are about 1% to about 40%, more preferably about 5% to about 35%, and even more preferably about 10% to about 30%, weight per volume (w/v). As used herein, "arabinogalactan, a biological or a functional equivalent thereof" includes an agent that is useful as a hematopoietic cell cryoprotective agent, and lacks the cytotoxic effect observed in the presence of DMSO. Thus, arabinogalactan, a biological or a functional equivalent thereof includes naturally occurring or synthetic arabinogalactan, portions of arabinogalactan, such as degradation products, and chemically (including those disclosed in U.S. Pat. Nos. 5,478,576 and 5,116,969, which are incorporated by reference herein) or biochemically modified arabinogalactan or portions thereof which have been modified using methods available in the art, which are effective in a somatic cell cryopreservation medium to protect somatic cell viability properties upon freezing and thawing of somatic cells in the medium. A "high survival rate" means that at least about 40%, preferably at least about 50%, more preferably at least about 60%, and even more preferably at least about 80%, of cryopreserved cells are viable upon thawing. The invention therefore provides a means to store and transport cells, e.g., adult hematopoietic cells such as lymphocytes, or fetal or neonatal hematopoietic stem or progenitor cells, which permits physicians and patients in rural areas or foreign countries to benefit from cellular therapies, and provides the opportunity to test donor cells for infectious agents.

Preferred hematopoietic cells for cryopreservation include peripheral blood lymphocytes, e.g., freshly isolated lymphocytes, activated, e.g., biologically activated, lymphocytes, or genetically modified lymphocytes, or stem cells, although the cryopreservation medium of the invention may be employed with any primary cell or cell line. In addition to arabinogalactan, a biological or a functional equivalent thereof, the cryopreservation medium preferably further comprises a cryoprotective agent that penetrates the cell membrane, e.g., glycerol or propylene glycol. The medium may also comprise a cryoprotective agent other than arabinogalactan or a biological or a functional equivalent thereof which does not penetrate the cell membrane.

The invention also relates to a composition suitable for administration to a human. The composition comprises a suspension of cells, e.g., hematopoietic cells, in a cryopreservation medium comprising a balanced electrolyte solution with at least one cryoprotective agent that is arabinogalactan, or a biological or a functional equivalent thereof. Preferably, the composition comprises between about $1 \times 10^4$ to $5 \times 10^8$ cells/ml. It is preferred that the composition is infusible.

Also embodied by the present invention is a method for preserving hematopoietic cells by contacting the cells with a cryopreservation medium comprising a balanced electrolyte solution and at least one cryoprotective agent that is arabinogalactan, or a biological or a functional equivalent thereof, to yield a cell suspension, which is subsequently frozen to yield a frozen cell suspension. Further provided is a frozen cell-containing composition prepared by the above described method.

DETAILED DESCRIPTION OF THE INVENTION

Definitions

Figure 1:
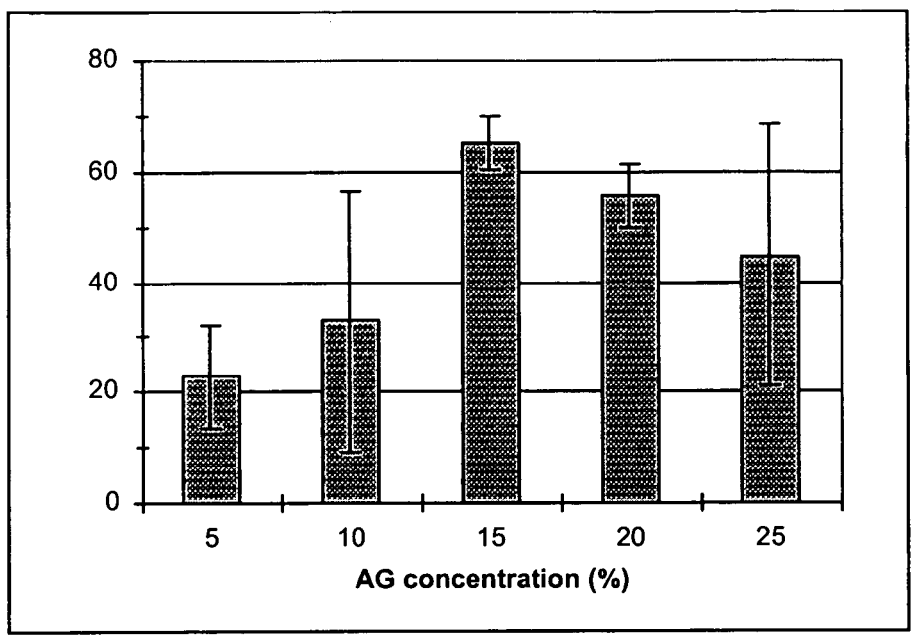
FIG. 1 depicts percent cell recovery as a function of arabinogalactan (AG) concentration for PBLs frozen at 5° C./minute in a solution containing Iscove's Modified Dulbecco's Medium (IMDM; Sigma, St. Louis, Mo.)+1% glycerol+x % AG. Error bars indicate the standard deviation of the measurement.

The terms "infusible" or "infusible-grade" refer to compounds, chemicals, solutions, compositions, mediums, agents, proteins or suspensions that are known to be safe, or have been determined to be safe for human use, e.g., by injection or infusion, and have preferably been approved for human infusion or injection by a United States regulatory agency, e.g., the FDA.

The term "balanced electrolyte solution" refers to balanced salt solutions composed primarily of inorganic salts. They contain no antimicrobial agents. Balanced salt solutions are used for fluid electrolyte replacement therapy, washing tissues and cells and as diluents for treating cells and tissues with various agents, while maintaining a physiological pH and osmotic pressure. Examples of electrolyte base solutions within the scope of the invention include, but are not limited to, lactated Ringer's solution, PlasmaLyte-A™, Normosol-R™, Veen-D™, Polysal®, plasma expanders such as 5% Dextran 40, IMDM, and Hank's Balanced Salt Solution (free from phenol red).

The term "cryopreservation medium" refers to a liquid medium (solution or suspension), capable of preserving structure and metabolism of isolated cells against injury associated with freezing events either within or exterior to the cells and that is safe for infusion or injection into humans. The term further refers to a medium (solution or suspension) containing components, including cryopreservation agents, also determined or known to be safe for human infusion or injection. Preferably, the medium (solution or suspension), and agents, components or elements of the medium are approved by a United States regulatory agency for infusion or injection into humans, e.g., histidine (50 mM).

"Cryoprotective agents" are agents that are capable of conferring a degree of cryoprotection to cell structure and metabolism upon freezing. Cryoprotective agents within the scope of the invention include arabinogalactan and biological and functional equivalents thereof, glycerol, propylene glycol, and albumin, e.g., human serum albumin, plasma or serum. Agents such as DMSO and Ficoll-hypaque are specifically excluded from being added to the infusible cryopreservation medium (solutions or suspensions) of the present invention.

The term "stem cell" or "hematopoietic stem cell" refers to a population of blood cells enriched in pluripotent cells which are uncommitted to a particular cell lineage and therefore retain the ability of self-renewal and the ability to differentiate into a specific lineage, such as "committed progenitor cells", i.e., lymphoid stem cells, which mature into B lymphocytes and T lymphocytes, myeloid or erythroid stem cells, which mature into red blood cells, granulocytes, monocytes and megakaryocytes. Alternatively, stem cells, and other hematopoietic cells can be obtained directly from a patient or donor's blood or blood forming tissues, e.g., peripheral blood, bone marrow, or umbilical cord blood.

The term "mononuclear cells" refers to any cell found in blood or blood forming tissues with a nucleus which is not segmented. These cells range from very primitive undifferentiated cells to mature cells, and include but are not limited to pluripotent stem cells, committed and uncommitted progenitor cells, lymphocytes and monocytes. Mononuclear cells can be obtained directly form a mammalian donor source or alternatively from a blood product source.

The term "physiological pH" refers to a pH, which is the measure of the acidity or alkalinity of a solution or composition, that numerically encompasses a neutral range of about 6.9–7.5, and more preferably about 7.2–7.5, and most preferably about 7.4–7.5.

The terms "tissue culture media components" or "cell culture media components" refer to known components of tissue or cell culture media. Such media include RPMI 1640, IMDM, AIM-5, X-VIVO 10, α MEM and other known tissue culture and cell culture media known to the art. These media, in addition to the usual small molecules, usually contain one or more specific proteins that most cells require in order to survive and proliferate in culture. These include growth factors that stimulate cell proliferation, and transferrin, which carries iron into cells. Several of these components are not safe for human injection or infusion, e.g., phenol red, or unavailable in U.S.P. grade.

The term "biological activity" refers to the viability or activity of stem cells, mononuclear cells and other hematopoietic cells removed from or contained within a suspension or cryopreservation medium that have undergone a freeze-thaw cycle or event, as compared to the viability or activity of cells that have not undergone a freeze-thaw cycle or event. Such viability or activity can be determined by assays such as those discussed hereinbelow. Cells having undergone a freeze-thaw cycle or event in suspension in the present media have at least about 20% to about 40% viability or activity when compared to non-frozen cells, preferably about 41% to about 55%, more preferably about 56% to about 70%, and most preferably about 71% to about 90% viability or biological activity.

The term "viability assay" refers to assays available to determine the viability or biological activity of mononuclear cells, stem cells and other hematopoietic cells and the percentage recovery of viable or biologically active cells removed from or contained within a suspension or cryopreservation medium after a freeze-thaw cycle or event. Aliquots from thawed samples can be tested by (1) membrane integrity assay using fluorescent markers such as acridine orange ("AO") and propidium iodine ("PI"), (2) a total cell count assay via a hemocytometer, or (3) proliferative capacity in culture, e.g., in liquid culture media or in methycellulose.

The term "controlled rate" refers to the temperature and speed, e.g., ° C./minute, a cell suspension is cooled after nucleation of the extracellular medium or solution.

"Freeze-thaw cycle or event" refers to subjecting a cryopreservation medium containing a suspension of mononuclear cells, stem cells and other hematopoietic cells to a cooling or freezing method, protocol, or regime at least once, and then subsequently subjecting it to a warming or thawing method, protocol, or regime.

The term "cell suspension" refers to a population or concentration of mononuclear cells, stem cells or other hematopoietic cells in a cryopreservation medium in either a liquid or frozen state.

The present invention provides a unique non-toxic cryopreservation composition comprising a polysaccharide cryopreservative, and a method of using the composition. A composition of the invention for use in the present invention may also include an agent that penetrates the cell membrane, such as, for example, glycerol or propylene glycol. Such cryoprotective agents are known to those of skill in the art. An alternate embodiment of the invention, however, is a cryopreservation medium with at least one cryoprotective agent that does not penetrate the cell membrane. Preferably, the cryopreservation composition does not include DMSO or a mixture of proteins, e.g., serum.

One class of polysaccharides includes arabinogalactans. Arabinogalactans are obtained from the cell walls of certain plants, particularly the American Western larch (*Larix occidentalis*). Arabinogalactan from Western larch has previously been used as a binder, stabilizer, and emulsifier in foods. Arabinogalactan derivatives and products are described in Jung et al. (U.S. Pat. No. 5,478,576) and Adams et al. (U.S. Pat. No. 5,116,969) and are included within the scope of "arabinogalactan, and biological and functional equivalents thereof."

Using arabinogalactan, the invention provides a non-toxic cryopreservation medium for hematopoietic cells. The medium includes a balanced electrolyte solution, the balanced electrolyte solution being composed of an appropriate concentration of sodium, potassium, and chloride to maintain normal osmolality, which incorporates the cryoprotective agent arabinogalactan, and may incorporate one or more other cryoprotective agents. The medium can be used for preserving a variety of cells, including peripheral blood lymphocytes. The cells may be freshly isolated lymphocytes, stem cells, activated lymphocytes, genetically modified lymphocytes, or a combination thereof.

The invention also provides a composition including a suspension of hematopoietic cells in a cryopreservation medium, the cryopreservation medium being a combination of a balanced electrolyte solution and at least one cryoprotective agent, including arabinogalactan or a biological or functional equivalent thereof. The hematopoietic cells may be peripheral blood lymphocytes, isolated lymphocytes, stem cells, activated lymphocytes, genetically modified lymphocytes, or a combination thereof from any mammal, particularly a human, or a bovine, canine, feline, ovine, murine, porcine, caprine, or equine. The composition can be infusible, and preferably does not contain DMSO. Preferably, the balanced electrolyte solution does not include protein, nor is the one or more cryopreservative agents composed in whole or in part of protein.

In the method of the present invention, hematopoietic or other cells are cryopreserved by contacting, e.g., resuspending, the cells with a cryopreservation medium of the invention to yield a cell suspension. The cell suspension is then frozen, using techniques such as those described below. The cells to be contacted include, but are not limited to, freshly isolated lymphocytes, stem cells, biologically modified lymphocytes, e.g., activated lymphocytes, genetically modified lymphocytes, or a combination thereof from mammalian blood or other tissue, particularly from human blood or tissue.

The invention also provides a frozen composition formed of a balanced electrolyte solution in combination with at least one cryoprotective agent and hematopoietic cells, e.g., peripheral blood cells or bone-marrow derived cells. The frozen composition can be formed by placing the hematopoietic cells in admixture with the balanced electrolyte solution and the at least one cryoprotective agent, e.g., arabinogalactan or a biological or functional equivalent thereof.

For cell therapy, hematopoietic cells may be genetically altered using a variety of methods known to those of skill in the art. These methods are generally grouped into four major categories: (1) viral transfer, including the use of DNA or RNA viral vectors, such as retroviruses (including lentiviruses), Simian virus 40 (SV40), adenovirus, herpes virus, alphaviruses, e.g., Sindbis virus, and bovine papillomavirus, for example; (2) chemical transfer, including calcium phosphate transfection and DEAE dextran transfection methods; (3) membrane fusion transfer, using DNA-loaded membranous vesicles such as liposomes, red blood cell ghosts, and protoplasts, for example; and (4) physical transfer techniques, such as microinjection, electroporation, or direct "naked" DNA transfer. Insertion of one or more pre-selected DNA sequences can be accomplished by homologous recombination or viral integration into the host cell genome. The desired gene sequence can also be incorporated into the cell, particularly into its nucleus, using a plasmid expression vector and a nuclear localization sequence. Methods for directing polynucleotides to the nucleus have been described in the art (Branden et al., 1999).

Calcium phosphate transfection, which relies on precipitates of plasmid DNA/calcium ions, can be used to introduce plasmid DNA containing a target gene or polynucleotide into isolated cells prior to cryopreservation. Briefly, plasmid DNA is mixed into a solution of calcium chloride, then added to a solution which has been phosphate-buffered. Once a precipitate has formed, the solution is added directly to cultured cells. Treatment with DMSO or glycerol can be used to improve transfection efficiency, and levels of stable transfectants can be improved using bis-hydroxyethylamino ethanesulfonate (BES). Transfection agents should be removed by gentle washing prior to contacting the cells with the cryopreservative medium of the present invention. Calcium phosphate transfection systems are commercially available (e.g., ProFection® from Promega Corp., Madison, Wis.).

DEAE-dextran transfection, which is also known to those of skill in the art, may be preferred over calcium phosphate transfection where transient transfection is desired, as it is often more efficient.

Since the cells to be cryopreserved are isolated from the body, microinjection can be effective for transferring genetic material into the cells. Briefly, cells are placed onto the stage of a light microscope. With the aid of the magnification provided by the microscope, a glass micropipette is guided into the nucleus to inject DNA or RNA. This method is advantageous because it provides delivery of the desired genetic material directly to the nucleus, avoiding both cytoplasmic and lysosomal degradation of the injected polynucleotide. Where hematopoietic or other progenitor cells are to be cryopreserved, the technique may provide enough genetically-altered cells to further expand in culture prior to or after cryopreservation by the method of the present invention.

Liposomal delivery of DNA or RNA to genetically modify the cells can be performed using cationic liposomes, which form a stable complex with the polynucleotide. For stabilization of the liposome complex, dioleoyl phosphatidylethanolamine (DOPE) or dioleoyl phosphatidylcholine (DOPC) can be added. A recommended reagent for liposomal transfer is Lipofectin®, which is commercially available. Lipofectin®, for example, is a mixture of the cationic lipid N-[1-(2,3-dioleyloyx)propyl]-N—N—N-trimethyl ammonia chloride and DOPE. Delivery of linear DNA, plasmid DNA, or RNA can be accomplished by liposomes, and can provide advantages due to the fact that liposomes can carry larger pieces of DNA, can generally protect the polynucleotide from degradation, and can be targeted to specific cells or tissues. A number of other delivery systems relying on liposomal technologies are also commercially available, including Effectene™ (Qiagen), DOTAP (Roche Molecular Biochemicals), FuGene 6™ (Roche Molecular Biochemicals), and Transfectam® (Promega). Cationic lipid-mediated gene transfer efficiency can be enhanced by incorporating purified viral or cellular envelope components, such as the purified G glycoprotein of the vesicular stomatitis virus enveloped (VSV-G), in the method described by Abe et al. (1998).

Viral vectors can be used to genetically alter cells prior to cryopreservation. Viral vectors can be used to delivery one or more target genes, polynucleotides, antisense molecules, or ribozyme sequences, for example, into the cells. Viral vectors and methods for using them to deliver DNA to cells are well known to those of skill in the art. Examples of viral vectors which can be used to genetically alter cells prior to cryopreservation include, but are not limited to, adenoviral vectors, adeno-associated viral vectors, retroviral vectors (including lentiviral vectors), alphaviral vectors (e.g., Sindbis vectors), and herpes virus vectors.

Retroviral vectors are most notably effective for transducing rapidly-dividing cells, although a number of retroviral vectors have been developed to effectively transfer DNA into non-dividing cells as well (Mochizuki et al., 1998). Packaging cell lines for retroviral vectors are known to those of skill in the art. Packaging cell lines provide the viral proteins needed for capsid production and virion maturation of the viral vector. Generally, these include the gag, pol, and env retroviral genes. An appropriate packaging cell line is chosen from among the known cell lines to produce a retroviral vector for transfer of DNA into hematopoietic or other cells prior to cryopreservation using the method of the present invention.

Successful transfection or transduction of hematopoietic cells prior to cryopreservation can be demonstrated using genetic markers, in a technique known to those of skill in the art. The green fluorescent protein of *Aequorea victoria*, for example, can provide an effective marker for identifying and tracking genetically modified hematopoietic cells in cell transfer.

Cryopreservation

Cryopreservation is the preservation of cell structure and metabolism against injury associated with freezing events within or around the cell. Natural cryoprotection can result from adaptive metabolism of the organism, with changes in cellular structure, composition and metabolic balance giving an enhanced tolerance of freezing. In laboratory experiments when cell viability or ultrastructure are to be preserved following cooling, two methods are available. The first is to ultra-rapidly cool the sample, resulting in the tissue fluids being vitrified, i.e., frozen in the absence of ice crystals. The second is to incorporate specific additives, e.g., cryoprotective chemicals or agents, to confer a degree of cryoprotection.

The first processing step in the cryopreservation of mononuclear cells, stem cells and other hematopoietic cells must be performed in such a way as to satisfy two essential criteria. First, the cells must not undergo irreversible damage due to the multiplicity of changes which occur within a sample during cooling. These changes include mechanical damage due to ice formation, cell-to-cell fusion due to the decrease in the solute volume available, and changes in acidity (pH) and salt or solute concentrations due to the segregation of solute and water. Second, the condition of the sample following cooling must be compatible with subsequent thawing and infusion procedures and requires specific attention to parameters such as sample size, ice forms created, and the nature and final concentration of additives or excipients. In satisfying these two criteria, the cryopreservation process represents a balance between the use of cryopreservation mediums and cryoprotective agents, to minimize changes during freezing by chemically increasing the volume of the ice free zone for a given cooling rate, and the cooling/freezing method itself.

Cryopreservation Medium

The cryopreservation medium of the instant invention employs an electrolyte base solution selected from the group consisting of lactated Ringer's solution, PlasmaLyte-A™, Iscove's Modified Dulbecco's Medium, Normosol-R™, Veen-D™, Polysal® and Hank's Balanced Salt Solution (containing no phenol red). These base solutions closely approximate the composition of extracellular mammalian physiological fluids. Normosol-R™ and Iscove's Modified Dulbecco's Medium are representative of the most preferred electrolyte base solutions for use in the present invention.

Lactated Ringer's solution is a sterile solution of calcium chloride, potassium chloride, sodium chloride, and sodium lactate in water suitable for injection. Lactated Ringer's solution contains about 130 mEq/liter of sodium (Na), about 4 mEq/liter of potassium (K), about 109 mEq/liter of chloride (Cl), about 3 mEq/liter of calcium (Ca), about 28 mEq/liter of lactate, and about 5 mEq/liter of glucose. (Lactated Ringer's solution is commercially available from Baxter, Hyland Division, Glendale Calif., Product No. 2B2073).

PlasmaLyte-A™ is a non-polymeric plasma expander and contains essential salts and nutrients similar to those found in culture medium but does not contain additional constituents found in tissue culture medium which are not approved for human infusion, e.g., phenol red, or are unavailable in U.S.P. grade. PlasmaLyte-A™ contains about 140 mEq/liter of sodium (Na), about 5 mEq/liter of potassium (K), about 3 mEq/liter of magnesium (Mg), about 98 mEq/liter of chloride (Cl), about 27 mEq/liter of acetate, and about 23 mEq/liter of gluconate. (PlasmaLyte-A™ is commercially available from Baxter, Hyland Division, Glendale Calif., product No. 2B2543).

Iscove's Modified Dulbecco's Medium (IMDM) is a sterile solution of calcium chloride, potassium chloride, and sodium chloride. (IMDM is commercially available from Gibco, Catalog No. 21056, which has no phenol red). IMDM contains about 1.5 mEq/L of calcium (Ca), about 4.4 mEq/L potassium (K), about 80 mEq/L chloride (Cl), about 114 mEq/L sodium (Na), about 0.8 mEq/L magnesium (Mg), and about 2.5 mEq/L of glucose.

Normosol-R™ is a sterile solution of magnesium chloride, potassium chloride, sodium chloride and sodium acetate, and also contains gluconate. Normosol-R™ contains about 140 mEq/liter of sodium (Na), 5 mEq/liter of potassium (K), 3 mEq/liter of magnesium (Mg), 98 mEq/liter of chloride (Cl), 23 mEq/liter of gluconate, and 5 mEq/liter of glucose. (Normosol-R™ is commercially available from Abbott Labs, Chicago Ill., product No. 796703).

Veen-D™ is a sterile solution of calcium chloride, potassium chloride, sodium chloride, and sodium acetate, and contains about 130 mEq/liter of sodium (Na), about 4 mEq/liter of potassium (K), about 109 mEq/liter of chloride (Cl), about 3 mEq/liter of calcium (Ca), about 27 grams/liter of acetate, and about 5 mEq/liter of glucose.

Polysal® is a minimum essential tissue culture medium ("MEM") that is a balanced polyionic electrolyte solution and contains about 140 mEq/liter of sodium, about 103 mEq/liter of chloride, about 5 mg/deciliter of calcium, about 3 mg/deciliter of magnesium, and about 55 mEq/liter of acetate maintained at a physiological pH. (Polysal® is commercially available from Cutter Biologicals, Emeryville Calif.).

Hank's Balanced Salt Solution (containing no phenol red) ("HBSS"), contains the inorganic salts potassium chloride (KCl), about 4 g/liter; potassium phosphate monobasic ($KH_2PO_4$), about 600 mg/liter; sodium chloride (NaCl), about 80 g/liter; sodium phosphate dibasic ($Na_2HPO_4$), about 475 mg/liter; and glucose, about 10 g/liter. HBSS is buffered with phosphate so that the solution will maintain its physiological pH under atmospheric conditions. For this reason it is the primary solution used in enzymatic treatments of cells and tissue and the final rinse of cells prior to the suspension of the cells in a complete growth medium. (HBSS is commercially available from Sigma Chemical Co., product H-1387.)

The cryopreservation mediums having an electrolyte base solutions as set forth above are preferably buffered by a buffering agent that has been approved for in vivo use in humans. Preferably, the base is buffered with histidine, e.g., at about 50 mM. In the present invention, the buffering agent is present in an amount effective to maintain a cryopreservation medium, solution, composition or cell suspension at physiological pH.

Cryoprotective Agents

Cryoprotective agents that can be used in the present invention range from naturally occurring cryoprotectants such as arabinogalactan, glycerol, propylene glycol, and albumin. Cryoprotective agents can be classified as penetrating and non-penetrating. Non-penetrating cryoprotective agents alter only the freezing characteristics of the extracellular medium whereas penetrating cryoprotective agents can modify both the intracellular and the extracellular medium composition.

The addition of a cryoprotective agent to a cell suspension can result in cellular damage if not introduced properly. It is well known that the addition of any solute changes the tonicity of a solution or medium. When cells are exposed to a high extra-cellular osmolarity, a cell can experience rapid ex-osmosis of water followed by a slow incorporation of a penetrating cryoprotective agent due to its lower permeability. Thus, the volumetric changes resulting from the fluxes of water and the addition of a cryoprotective agent can result in damage to the cells. Tissues and intact organs can experience reduced cell viability and biological activity when exposed to sufficiently large step changes in external osmolarity resulting from improper introduction of a cryoprotective agent (Pegg, 1972).

Typically, mediums containing cryopreservation agents are introduced using step-wise increments of increasing concentration in order to avoid cellular osmotic shock associated with single-step introduction or removal. For example, a cryopreservation medium can be prepared by adding a cryoprotective agent to first create an "intermediate" concentration and then slowly increased via a slow drip method or other similar method, to achieve a desired concentration of a cryoprotective agent. Alternatively, a cryoprotective agent can be added entirely by a slow drip method to avoid cellular damage. Additionally, prior to infusion of a thawed cell suspension in a medium of the present invention, a cryoprotective agent can be "removed" by diluting the medium with another medium free of cryoprotective agents until a desired concentration is achieved that is suitable for infusion into a patient.

Not only are large increases in a medium or solution's osmolarity potentially damaging, but long term exposure to even low cell concentrations of certain cryopreservation agents, such as DMSO, at room temperature can be lethal (Fahy et al., 1990). It is believed a reduction in temperature can suppress the kinetics of cell damage associated with exposure to a cryoprotective agent while also suppressing a "rapid" permeation of cryoprotective agents into a cell. Additionally, exposure of cells to certain cryoprotective agents (DMSO in particular) has been associated with loss in cell viability and activity with extended exposure. Studies have quantified specific cellular changes resulting from exposure to a cryopreservation agent such as DMSO. These studies have showed cellular damage that includes cytoskeletal reorganization, cross-linking of nuclear proteins and alterations in membrane permeability (Fahy et al.), and can account for loss in cell viability and activity. The toxicity of cryopreservation agents such as DMSO, has led to the development of the improved methods described herein.

The primary factors affecting the cryoprotective nature of an agent are (a) chemical nature, (b) relative lack of toxicity, (c) molecular size and penetrating ability, and (d) interaction with other compounds in the mixture. In the present invention it is preferred that only infusible-grade cryoprotective chemicals or agents are employed. Thus, preferred cryoprotective agents of the instant invention include arabinogalactan, glycerol, hydoxyethyl starch, and human serum albumin, as these agents are suitable for infusion or injection into humans, e.g., infusible grade.

The physicochemical effects of cryoprotective agents are (a) depression of the equilibrium freezing point of substrate and cytoplasm on a colligative basis, (b) depression of homogeneous ice nucleation temperature, (c) reduced rate of ice crystal growth due to change in the viscosity and thermal diffusivity of the solution, and (d) dehydrative effects on cells by osmotic action.

The action of glycerol has been interpreted as penetrating and exerting colligative action within the cells. In the proportion that the colligative action of glycerol maintains water in the liquid state at temperatures below 0° C., an increased volume of cellular solution is maintained. This avoids an excessive concentration of toxic electrolytes in the non-frozen cellular solution. A similar influence also takes place in the external solution. In this context, colligative action is referred to as action by an extraneous solute, in lowering the freezing point of the solution in contact with ice. If enough glycerol is present, the salt concentration does not rise to a critically damaging level until the temperature becomes so low that the damaging reactions are slow enough to be tolerated by the cells.

However, the use of glycerol concentrations of 6% or greater can employ a multi-step addition or removal of glycerol, as described above, in order to minimize the loss of cells due to osmotic shock. It is expected that higher cell viabilities can be observed with increased concentration levels of glycerol, although higher glycerol concentrations can require additional processing, e.g., multi-step addition or removal to a cell suspension and require a slower cooling rate. Glycerol is used in the cryopreservation medium of the present invention, in a concentration of about 0.5% to about 20%, preferably about 0.75% to about 10%, more preferably about 1% to about 6%, and even more preferably about 1% to about 5%.

Non-penetrating cryoprotectants vary in size from human serum albumin, to large polymeric substances such as polyvinylpyrrolidone (PVP), arabinogalactan, dextran and modified starches such as hydroxyethyl starch (HES). It has been suggested that non-penetrating substances act by some other means rather than that in the colligative mechanism described above. The role of larger molecules is believed to be dehydrative by osmotic action. When a large proportion of water is withdrawn from the cells by means of an osmotic differential, less free water is available for intracellular ice crystallization which is often identified as a lethal factor.

Human serum albumin (HSA) is also classified as a non-penetrating cryoprotectant. Human serum albumin is a sterile, non-pyrogenic preparation of serum albumin that can be obtained by fractionating blood, plasma, serum or placentas from healthy human donors. The albumin content is not less than 96% of the total protein. HSA may contain sodium acetytryptophanate alone, or with sodium caprylate as a stabilizing agent. The sodium content is not less than 130 mEq/liter and not more that 160 mEq/liter and contains no microbial agents. HSA is used in a cryopreservation medium of the present invention in a concentration range of about 0.5% to about 12%, preferably about 1% to about 10%, and most preferably about 3% to about 6%.

Stem cells, mononuclear cells and other hematopoietic cells can be obtained from normal human donors stimulated with granulocyte-colony stimulating factor ("G-CSF"). Donors can be administered G-CSF, for example 5–12 μg/kg for a period of 1–6 days, and an apheresis product can then be collected. Generally, an apheresis product is purified and rich in mononuclear cells, but if additional cell purification or processing is desired, density gradient separation techniques and centrifugation techniques well known to the art can be implemented.

Alternatively, stem cells, mononuclear cells and other hematopoietic cells can be obtained from other methods employing positive and negative selection techniques. For example, cells can be obtained from mammalian bone marrow, as from human bone marrow, e.g., by centrifugation and the immunomagnetic and FACS procedures as described in Verfaillie et al., 1990. This procedure yields cell populations highly-enriched in human stem cells which are characterized by being $Lin^-$ $CD34^+DR^-$. Other hematopoietic cell populations having enriched stem cells include the $CD34^+$ population disclosed by Civin (U.S. Pat. No. 4,714,680), the $CD34^+$, $CD38^-$ population disclosed in European patent application No. 455,482, the population disclosed by Tsukamato et al. (U.S. Pat. No. 5,061,620). See also, Champlin, 1995; Noga, 1992; Preti et al., 1993; *Bone Marrow and Stem Cell Processing: A Manual of Current Techniques*, edited by Areman et al., F. A. Davis Company (1992), as well as a population of $CD34^-$ cells. Upon the isolation and purification of cells, the cells can be added or suspended in the cryopreservation medium of the invention.

Final cell volume and cell concentration in a cryopreservation medium is important in the development of a freezing method for stem cells, mononuclear cells and other hematopoietic cells. Previous studies have observed that the viability of cells which are frozen and thawed can be adversely effected when the concentration of cells exceed a 20% cytocrit. (Nei, 1981). Thus, in the present invention, using an approximate cell diameter of 20 μm, the final cell concentration in a cryopreservation medium should not exceed about $1 \times 10^9$ cells per ml of medium. Additionally, in order to minimize the load on the cardiovascular and renal systems, it is desirable to reduce the overall volume of medium infused into a human patient which requires maximizing the cell concentration used. Thus, stem cell, mononuclear cell and other hematopoietic cell suspensions are prepared in accordance with the present invention by providing a population of isolated and purified stem cells, mononuclear cells and other hematopoietic cells, and introducing them into a cryopreservation medium. In the present invention, the cell concentration can average about $1 \times 10^4$–$1 \times 10^9$ cells/ml of medium, preferably about $2$–$5 \times 10^7$ cells/ml of medium, and most preferably about $3 \times 10^7$ cells/ml of medium.

Controlled Freezing

The selection of a cryopreservation medium and a subsequent freeze-thaw method, so as to result in optimum survival rate of stem cells, mononuclear cells and other hematopoietic cells, are not independent events. The composition of a particular cryopreservation medium influences the cooling rate at which maximum cell survival is observed. Cryoprotective agents that do not penetrate the cell membrane, do not appear to have a strong influence on the optimum cooling rate of a cryopreservation medium. Glycerol, however, plays an important role in the cooling rate at which maximum cell survival is observed.

Normally, cooling rates that are slightly below the threshold cooling rate for intracellular ice formation are preferred. Intracellular ice formation can occur because there is insufficient time for water to escape from the cells before the contained cell water freezes. With cooling rates that are slightly below the threshold cooling rate for intracellular ice formation, extracellular ice forms first, resulting in dehydration of the cell which, together with the presence of the cryoprotectant, prevents intracellular ice formation.

A variety of cooling methods can be used for the cryopreservation of stem cell, mononuclear cell and other hematopoietic cell suspensions of the instant invention. In a preferred embodiment of this invention, the cooling rate that a cryopreservation medium containing a cell suspension experiences before the extracellular medium or solution has formed ice, is not a critical factor, as stem cells, mononuclear cells and other hematopoietic cells do not normally exhibit cold shock behavior. However, once ice formation in the extracellular solution has occurred, the cryopreservation medium of the present invention represents an improvement over current mediums exposed to a variety of freezing methods. As previously stated, after the formation of ice in the extracellular medium, current freezing methods employ a final cooling rate of about 1° C./minute, whereas the cryopreservation medium of the instant invention can be cooled at faster final cooling rates, preferably about 5° to 10° C./min while maintaining cell viability and achieving higher cell yield than conventional cryopreservation mediums exposed to known freezing methods. Current cryopreservation mediums, e.g., DMSO containing mediums, lyse many cells during the freezing process, and ultimately yield much lower cell counts than the mediums of the present invention. Although DMSO mediums yield fairly high viability yields, the total cell count after a freeze-thaw cycle or event is usually low.

An alternative cooling method of the instant invention, employs controlled cooling prior to the formation of ice in an extracellular medium. In a preferred embodiment, a population of cells are suspended in a cryopreservation medium at a temperature of about 4° to 37° C., allowed to equilibrate and then cooled in a 5 step method. Step 1 involves cooling the cell suspension from about 0° C. to about −8° C. at a cooling rate of about −1° C./minute. At a temperature of about −8° C., the cell suspension is typically still undercooled and no ice has formed in the extracellular solution. Step 2 involves cooling the cell suspension from about −8° C. to about −45° C. at a cooling rate of about 50° C./minute. The extracellular solution should form ice during this step. Step 3 involves warming the cell suspension from about −45° C. to about −12° C. at a warming rate of about 15° C./minute to induce nucleation of the extracellular solution, e.g., ice crystals form in the extracellular solution resulting in a release of the latent heat of fusion. Step 4 involves cooling the cell suspension at a controlled cooling rate of about 1 to 20° C./minute to a final temperature of about −60° C. Step 5 includes cooling the suspension at a controlled cooling rate of about 3° C./minute to a final temperature of about −100° C.

Any volume of a cell suspension may be subjected to the cooling method of the invention. For example, 1.0 ml of a cell suspension at a cell concentration of about $2$–$5 \times 10^7$ cells/ml of cryopreservation medium in cryogenic vials (Corning Costar Corporation, Cambridge, Mass. 02140), or 10 ml of cell suspension at a cell concentration of about $2$–$5 \times 10^7$ cells/ml of cryopreservation medium in Cryocyte™ 50 bags, may be employed. A 10 ml volume of a cell suspension would be typical of that used in the freezing of umbilical cord blood or other immunotherapy products.

The final storage temperature of a cell suspension is typically determined by the glass transition temperature of the cryopreservation medium. Thus, the present invention provides that a cell suspension should be cooled below the glass transition temperature of the extracellular medium so that the cell suspension is completely solidified at the end of the method. For the cryopreservation mediums of the present invention, the glass transition temperature is between about −70° to −198° C., and preferably about −80° to −120° C.

Uncontrolled Freezing

Uncontrolled freezing refers to the freezing of a cell suspension in a cryopreservation medium exposed to a fixed low temperature, i.e., that has been placed in a mechanical freezer capable of holding a specified temperature, e.g., −80° or −153° C. The suspension will cool at a variety of cooling rates due to heat transfer characteristics of the freezer and cell suspension. Thus, the formation of ice in the extracellular medium is not controlled. However, it is possible to determine from the slope of a temperature versus time plot, the approximate cooling rate after the formation of ice in the extracellular medium, as indicated by the release of a majority of the latent heat of fusion which is measured by thermocouples and recorded on a data logging instrument, e.g., a strip chart recorder. Uncontrolled freezing methods are popular in a variety of smaller hospitals and in Europe, and in a variety of clinical and military applications. Freezing of stem cell, mononuclear cell and other hematopoietic cell suspensions in these situations is typically performed in −80° or −153° C. mechanical freezers. Biochemical activity of cells is suppressed below −153° C.

Storing and Thawing

In a preferred embodiment, cell suspensions are cooled so that ice crystal formation occurs below the temperature that would cause damage to the cells. Once frozen, the suspension is stored below the glass transition temperature of the most unstable ice form. For amorphous ice, this is preferably below −160° C. Stem cell, mononuclear cell and other hematopoietic cell suspensions may be stored indefinitely prior to thawing.

Preferably, the thawing of a cell suspension is accomplished by placing the cell suspension in a water bath until all visible ice crystals in the cryopreservation medium have disappeared. This thawing method is designed to result in the rapid thawing of the cell suspension and intended to minimize recrystallization or osmotic injury experienced during the rewarming phase of the method. Preferably, the water bath is maintained at a temperature of about 37° to 42° C., and most preferably at 37° C.

Measuring Biological Activity

In a preferred embodiment of the invention, a variety of in vitro assays can be performed in order to assess viability and percent recovery of stem cells, mononuclear cells and other hematopoietic cells from a cryopreservation medium. Upon thawing, a cell suspension is mixed using a syringe, or other suitable means, to ensure even distribution of cells. Aliquots from the thawed suspension can be removed and assayed to determine: (1) membrane integrity of cells using fluorescent markers, such as acridine orange (AO) (Sigma, St. Louis, Mo.), and propidium iodine (PI) (Sigma, St. Louis, Mo.); (2) total cell count using a hemocytometer; (3) proliferative capability of the cells in a methylcellulose culture supplemented with cytokines, and; 4) flow cytometry for cells that are CD $34^+$ $45^+$.

Frozen-thawed samples of stem cell, mononuclear cell and other hematopoietic cell suspensions in a cryopreservation medium are mixed using a syringe to ensure even distribution of cells. Aliquots from the samples are removed and in vitro viability assays were performed to assess the viability and percentage recovery of cells.

To determine membrane integrity using AO/PI, 5 µl of cell suspensions are diluted with 95 µl of IMDM. Equal amounts of cell suspension and AO/PI solution were added and the suspension was placed on the hemocytometer and cells were counted using fluorescent microscopy (Zeiss Axioskop, Germany). Cells which fluoresced green were considered viable wherein cells that fluoresced red/orange were considered dead. By determining the total number of cells within a given region of the hemocytometer, it was possible to determine a cell concentration which when multiplied by total volume resulted in a total cell number in a suspension.

To determine proliferative capability of cells, an aliquot of cell suspensions are centrifuged at 500×g for 2 minutes and the supernatant was removed. The pellet is resuspended in IMDM to a final concentration of $2 \times 10^6$ viable cells/ml. Subsequently, $2 \times 10^4$ and $5 \times 10^4$ cells are added to 1 ml of MethoCult™ (Stem Cell Technologies, Vancouver, BC), methylcellulose culture medium for cells. The mixture is supplemented with IMDM+2% fetal calf serum (Gibco, Grand Island, N.Y.), mixed and pipetted into 35×10 mm petri dishes (Falcon, Plymouth, England). The cultures are then placed in a misted air incubator for 2 weeks and colony formation was determined. Colonies were scored for CFU-GM, CFU-GEMM and BFU-E and the total number of colonies are counted. The total colony numbers for a given seeding density are determined. The percentage colony recovery is determined by dividing the total number of colonies counted post freeze-thaw by that obtained in the pre-freeze product for the same cell seeding density.

Similarly, experiments are performed on pre-freeze samples as a direct control. These assays permit a determination of the total viable cell yield (total viable number of cells post freeze-thaw divided by the total number of viable cells pre freeze-thaw), the cells expressing membrane integrity, and the proliferative capability of the cells.

The fraction of cells which expressed the CD 34 antigen may be determined for both the fresh samples and frozen/thawed cells. Cells are stained with an antibody for CD 34 (Beckton Dickinson, San Jose, Calif.) and an antibody for CD 45 (Dako Corporation, Carpinteria, Calif.). The fraction(s) of cells that are CD $34^+$ was determined using flow cytometry.

The invention will be further described by the following example.

EXAMPLE 1

Methods

Isolation of Peripheral Blood Mononuclear Cells

Whole blood units (approximately 450 ml, with heparin anticoagulant) were obtained from healthy donors through standard venipuncture. Venipuncture was performed by the staff of the University of Minnesota Hospital Blood Bank Donor Center, with informed consent from all donors. The entire unit of blood was centrifuged at 4500 g for 4 minutes at room temperature. A buffy coat was prepared by extracting (and discarding) the plasma, then collecting approximately 50 ml from the top of the pelleted cells. The buffy coat was diluted with an equal volume of Dulbecco's Phosphate Buffered Saline (PBS) (Celox Laboratories Inc., St. Paul, Minn.).

Mononuclear cells (MNCs) were isolated from the samples using density gradient purification. Briefly, twenty ml of Histopaque-1077 (Sigma Chemical Co., St. Louis, Mo.) was added to each of four 50 ml centrifuge tubes. A 25 ml aliquot of diluted buffy coat was carefully overlaid. The tubes were centrifuged at 400 g for 30 minutes at room temperature. After discarding the upper layer, the band of mononuclear cells were collected by pipette. Cells were washed with 100 ml Iscove's Modified Dulbecco's Medium (Sigma).

Culture and Transduction

Aliquots of the PBLs from a donor with mucopolysaccharidosis type II (MPS II), also known as Hunter's syndrome, were thawed and resuspended in wash solution containing Minimal Essential Media (MEM, Gibco) supplemented with 1% HSA, 20,000 units of heparin (Schein Pharmaceutical, New York) and Deoxyribonuclease I (DNAse, Sigma). After completion of the wash protocol, the cells were resuspended in a culture medium containing AIM-V (Gibco) supplemented with 5% fetal bovine serum, 0.4 mM L-glutamine (Gibco) and recombinant Interleukin-2 (rIL-2, R&D Systems, Minneapolis, Minn.). On the first day of culture only, the cells were supplemented with OKT3 (Ortho Biotech, Raritan, N.J.) to a final concentration of 50 ng per $1 \times 10^7$ cells. The cells were precultured for 3 days in a Lifecell bag (Baxter Healthcare, Deerfield, Ill.) and then inoculated into the lumen space of a hollow fiber bioreactor (HFBR, Cellmax, Artificial Capillary Module for Lymphocytes, Cellco, Germantown, Md.) with a total lumen volume of 11 ml.

After 24 hours, the cells were transduced with retroviral vector L2SN that contained the cDNA encoding human iduronate-2-sulfatase under the transcriptional regulation of the LTR and the neomycin phosphotransferase gene regulated by the simian virus 40 (SV40) early promoter (Pan, 1997). The cells were transduced once per day for the next four days. After approximately 4 days of culture in the HFBR, the cells were harvested and inoculated into a HFBR with a total lumen volume of 60 ml to permit further expansion of the genetically modified PBLs. The cells were cultured for an additional 7 days in the large HFBR and then harvested, washed and administered as a part of a clinical gene therapy trial. The total protocol including bag preculture and culture in the medium and large HFBR lasted 15 days (Stroncek et al., 1999). Cells in excess of the specified dose for the clinical trial were used in the following experiments.

Activation of PBLs

PBLs from normal donors were activated using a brief period of ex vivo culture. The PBLs obtained from density gradient separation were resuspended in AIM-V (Gibco) at a density of $10\times10^6$ cells/ml in a total volume of 100 ml. The culture medium was supplemented with rhIL-2 at a concentration of 1000 IU/ml (Chiron). The cells were incubated for 18 hours at 37° C. and 5% $CO_2$. Control cultures were also maintained under the same conditions (cell density, AIM-V culture medium) without exogenous IL-2 added to the cultures.

Cryopreservation Studies

The response of the MNCs to a freeze-thaw cycle was determined through a series of controlled-rate freezing experiments. The MNCs were centrifuged at 500×g for 10 minutes and resuspended in a selected cryopreservation solution. The final pre-freeze cell concentration was specified to be between $20$–$50\times10^6$ cells/ml. MNCs were frozen in 2 ml cryovials (Nunc, Napierville, Ill.) or cryocyte-50 bags (working volume of 10 ml). Approximately 10 ml of cell suspension was transferred into a freezing bag (Cryocyte, Baxter, Round Lake, Ill.) and sealed (Sebra Tube Sealer, Sebra, Tucson, Ariz.). The bag was placed in a press and placed vertically in a controlled rate freezer (Planar 10/16, Kryo Med, UK).

The bags were frozen by cooling the sample from room temperature to 0° C. at 10° C./minute. The samples were then held for 15 minutes to permit equilibration. The samples were then cooled at 1° C./minute to −8° C., 50° C./minute to −45° C. and allowed to warm at 15° C./minute to −12° C. to facilitate seeding of ice in the extracellular solution. The samples were then frozen at the specified cooling rate (1 to 10° C./minute) to a temperature of −60° C., then at a rate of 3° C./minute from −60° C. to −100° C. After reaching −100° C., the samples were removed from the controlled rate freezer and placed in a liquid nitrogen storage dewar (Model XLC-230, MVE, Bloomington, Minn.). At a time of no greater than 6 months with an average of approximately 3 weeks, the cells were removed from storage and thawed. The sample was placed in a 37° C. water bath and gently agitated until all visible ice crystals had disappeared. The cells were transferred into a sterile centrifuge tube and an equal volume of IMDM was added to the cell suspension to dilute the cryopreservation solution.

Additional studies were performed to determine the post-thaw viability of cells frozen in a mechanical freezer (−80° C.). For these studies, approximately 10 ml of cell suspension in the solution of interest was added to a Cryo-Cyte 50 bag (Baxter, Deerfield, Ill.). The bag was heat sealed (Sebra Tube Sealer, Tucson, Ariz.), placed in a bag press and inserted into a metal frame located in a −80° C. mechanical freezer (Harris Scientific, Rochester, N.Y.). The metal frame was placed vertically in the −80° C. mechanical freezer and supported at the bottom by a stand made of styrofoam. The frame containing the bags and presses was not in contact with the bottoms, sides or top of the −80° C. freezer and no other products were touching the rack containing the bags during the freezing process. This protocol was developed to reduce uncontrolled heat removal from the sample and enhance the reproducibility of the freezing protocol. For specific experiments, the bag press was insulated to reduce the cooling rate of the sample in the bag. Bags containing the cryopreservation solution of interest (but no cells) were instrumented with thermocouples. The temperature as a function of time for each sample was recorded and analyzed after completion of the freezing process. The cooling rates that could be obtained using uninsulated and insulated bags was approximately 1.4, 3.8 and 6.3° C./minute. This range of cooling rates was comparable to those tested using the controlled rate freezer.

Post-Thaw Viability

Immediately post-thaw, the viability of the cells was determined using fluorescent dyes (Acridine orange and propidium iodine, AO/PI). Approximately, 5 µl of cell suspension was diluted with 95 µl of IMDM. Equal amounts of cell suspension and AO/PI solution (Sigma) were added and the sample was placed on the hemocytometer and counted using fluorescent microscopy (Zeiss). Samples that fluoresced green were considered viable while those cells that were red/orange were considered nonviable. By determining the total number of cells within a given region of the hemocytometer grid, the total number of cells (dead and alive) was determined.

The viability of the frozen-thawed cells was also determined 48 hours post-thaw. Previous studies using freshly isolated cells from a donor with MPS II that were cryopreserved, thawed, and then cultured and transduced, indicated that the post-thaw viability of the cells was at its minimum at 48 hours post-thaw (Shankar, 1997). Thus, the viability measured at 48 hours post-thaw is the minimum viability expected. The post-thaw cultures were performed by taking approximately $5\times10^6$ cells from the cell suspension and pelleting the cells at 500×g for 1 minute. The supernatant was removed and replaced with 1 ml of culture medium consisting of RPMI 1640 (Gibco) supplemented with 5% fetal bovine serum (Gibco) and 20 mM 2-mercapto-ethanol (βME). Aliquots of 200 µl were transferred to triplicate wells of a 96-well tissue culture plate (Costar Corp., Cambridge, Mass.) and incubated at 37° C. and 5% $CO_2$. After 48 hours, the plates were removed from the incubator. The cells were resuspended using a pipette and the viability and total cell counts determined using a hemocytometer.

Data Analysis

Statistical analysis of the data was performed using StatView software (SAS Institute, Cary, N.C.). Viability and cell recovery were analyzed using an unpaired t-test.

Results

Cryopreservation of PBLs from Normal Donors

The development of a cryopreservation protocol for lymphocytes in solutions containing AG requires the determination of solution composition and cooling rate for these cells. The influence of composition changes in the post-thaw viability of lymphocytes using different AG-based cryopreservation solutions (Table 1) was determined. The optimum concentration of AG was determined by starting with a solution containing 1% glycerol in IMDM and varying the AG concentration (ultrarefined AG was obtained from Larex Corp., St. Paul, Minn.). The cooling rate for these experiments was kept constant (5° C./minute). The overall recovery, defined as the number of viable cells 48 hours post-thaw divided by the number of viable cells initially as a function of AG concentration, was determined (FIG. 1). These results indicate that for the cooling rate and glycerol composition tested, 15% AG was the concentration associated with highest survival for the solution compositions tested. The difference in overall recovery between 10, 15, and 20 w/v % AG were marginally statistically significant (p=0.0901). This composition also permitted centrifugation of the cells, filtration of the solution through 0.22 μm filters for sterilization and rapid incorporation of AG into solution during formulation. Thus, from both a solution processing and post-thaw processing standpoint, this concentration of AG was favorable.

TABLE 1

Cryopreservation Solutions

| Solution | AG (%, w/v) | glycerol (%, v/v) | DMSO (%, v/v) | 25% HSA (%, v/v) | base solution |
|---|---|---|---|---|---|
| L1 | 25 | 0 | 0 | 1 | IMDM |
| L1' | 25 | 0 | 0 | 0 | IMDM |
| L2A05 | 5 | 1 | 0 | 1 | IMDM |
| L2A10 | 10 | 1 | 0 | 1 | IMDM |
| L2A15 | 15 | 1 | 0 | 1 | IMDM |
| L2A20 | 20 | 1 | 0 | 1 | IMDM |
| L2 | 25 | 1 | 0 | 1 | IMDM |
| L2' | 25 | 1 | 0 | 0 | IMDM |
| L3 | 25 | 0 | 5 | 1 | IMDM |
| L4 | 0 | 1 | 0 | 1 | IMDM |
| L5 | 0 | 0 | 5 | 1 | IMDM |
| L6 | 15 | 3 | 0 | 0 | IMDM |
| L7 | 15 | 3 | 0 | 0 | Normosol-R ™ |

The cryoprotective benefits of proteins, such as HSA, in the cryopreservation of hematopoietic cells is well documented. Traditionally, autologous serum or HSA has been used in cryopreservation solutions for hematopoietic cells. Nevertheless, autologous serum may be removed during ex vivo manipulation of cultured, genetically modified cells. Moreover, autologous serum may not be appropriate for use in cryopreservation of a cellular therapy for certain diseases, or due to the presence of residual drugs. Although HSA is the most frequently used source of protein in cryopreservation solutions when autologous serum is not available (Rowley, 1992), this source of protein is relatively expensive and may represent a potential source for the transmission of disease agents as it is manufactured from pooled sources.

Figure 2:
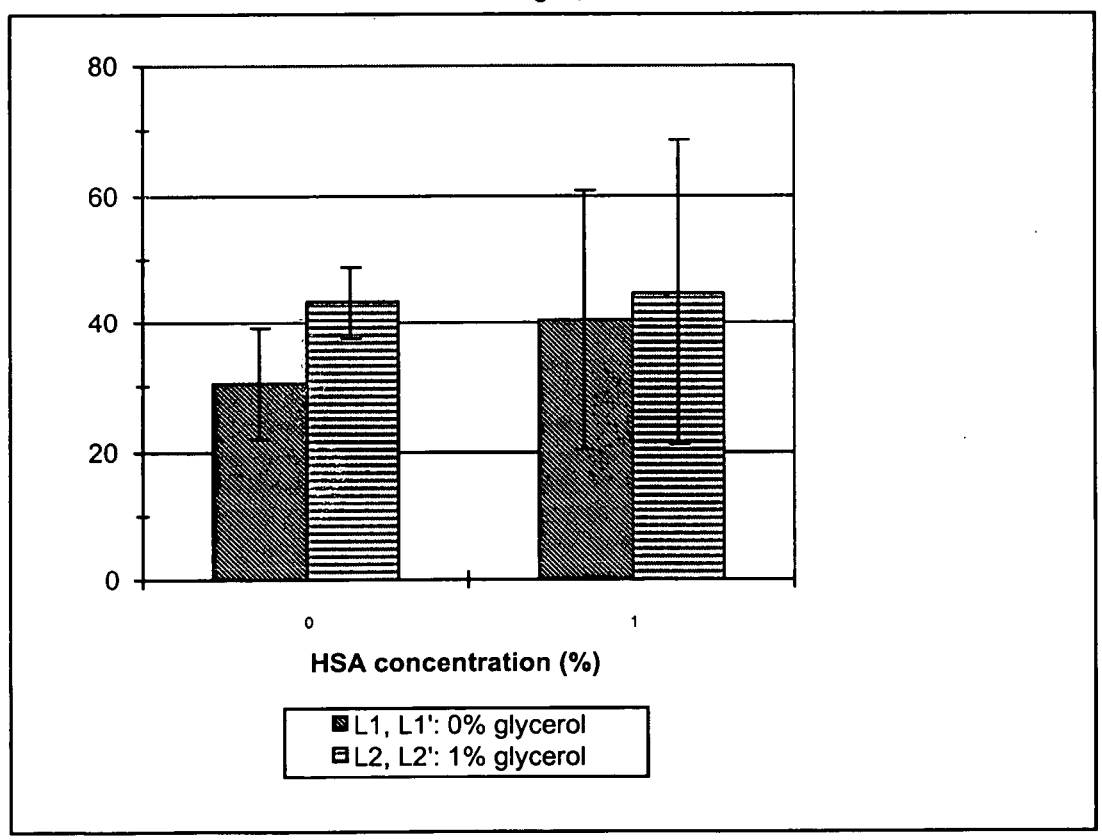
FIG. 2 illustrates percent cell recovery as a function of human serum albumin (HSA) concentration for PBLs frozen at 5° C./minute in (1) 25% AG with or without 1% HSA, and (2) 25% AG and 1% glycerol with or without 1% HSA. Error bars indicate the standard deviation of the measurement.

To determine the optimum concentration of HSA in a cryopreservation solution containing AG, and whether serum-free formulations provide comparable survival to those containing AG, two different compositions were studied: (1) 25% AG with or without 1% HSA; and (2) 25% AG and 1% glycerol with or without 1% HSA. For a cooling rate of 5° C./minute, cell recovery as a function of HSA composition was determined for the two solutions of interest (FIG. 2). The differences in overall recovery with and without HSA were not statistically significant for both 0% glycerol (p=0.4811) and 1% glycerol (p=0.9136). These results indicate that solutions containing AG do not require HSA.

Figure 3:
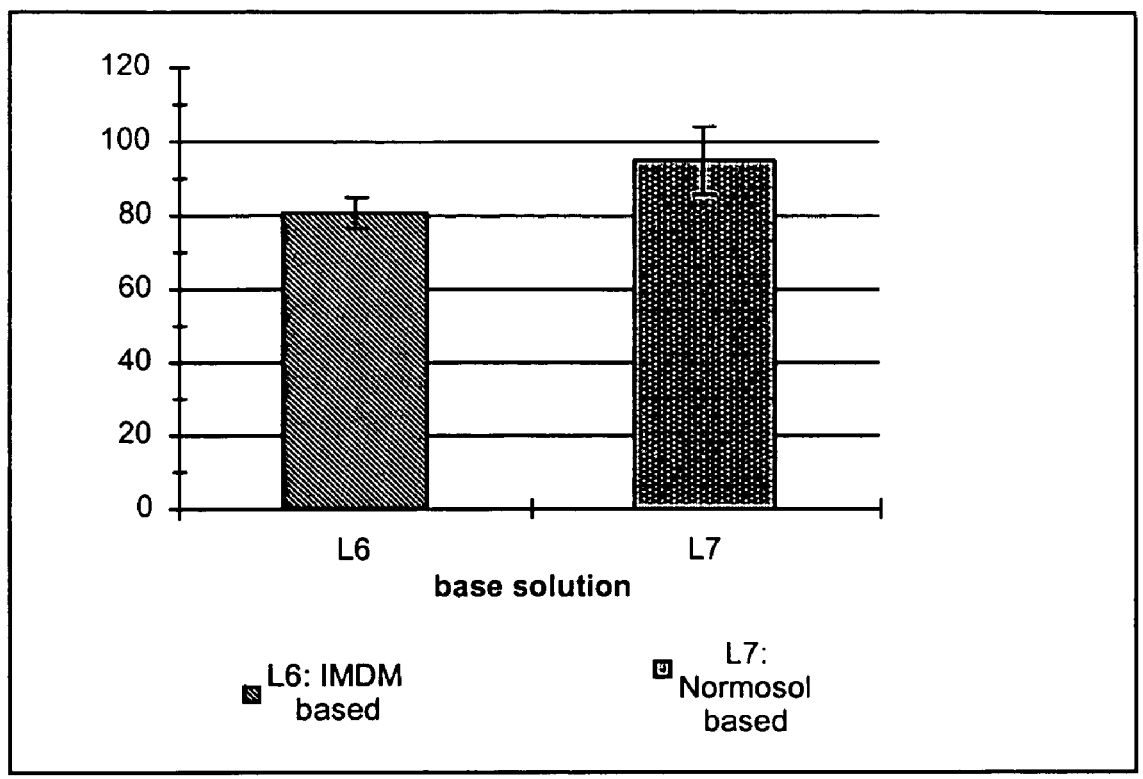
FIG. 3 depicts percent cell recovery for PBLs from a normal donor cryopreserved in a solution containing 3 v/v % glycerol+15 w/v % AG with IMDM or Normosol-R™ as the base of the cryopreservation solutions. The cells were frozen at a cooling rate of 5° C./minute.

As indicated previously, there is considerable interest in lymphocytes for human therapeutic purposes. Previous studies have used a tissue culture medium, IMDM, as the base for a cryopreservation solution. Other studies have shown that balanced electrolyte solutions routinely used for human infusion can be used as a base for cryopreservation solutions (Fraser, 1998). To compare the post-thaw viability for solutions containing IMDM and Normosol-R™, a solution approved for human infusion of PBLs, PBLs were resuspended in a solution containing 3 v/v % glycerol+15 w/v % AG and IMDM or Normosol-R™ as the base of the cryopreservation solution and frozen. The cell recovery for the solutions using the two different bases was slightly higher for solutions containing Normosol-R™ (FIG. 3). The differences in viability were determined to be statistically different (p=0.0665). These results indicate that using Normosol-R™ results in higher post-thaw viabilities.

In many hospitals or clinics, controlled-rate freezers are not available. Cells are typically cryopreserved in mechanical freezers (−80° C.) using uncontrolled cooling. The cooling rates in a mechanical freezer at −80° C. are comparable to those used in previous controlled rate experiments (1–7° C./minute). The cooling rate achieved for a 10 ml sample in a Cryocyte bag contained in the metal press/racking system described above was approximately 6° C./minute. If additional layers of insulation were added, cooling rates of 4 and 1° C./minute could be obtained.

PBLs resuspended in a solution containing 3 v/v % glycerol+15 w/v % AG+Normosol-R™ were frozen in a −80° C. mechanical freezer. The samples were frozen in uninsulated or lightly insulated bags to achieve a range of cooling rates comparable to that studied in the controlled rate freezing studies. For comparison, cells were also frozen in 10 v/v % $Me_2SO$ solution. The postthaw cell recovery of cells frozen at approximately 4° C./minute (100±24%) was comparable to that obtained using the same solution in a controlled-rate freezer at a cooling rate of 5° C./minute (95±9%) (p=0.702). Freezing of the PBLs at a higher cooling rate (6° C./minute) reduces the cell recovery observed significantly (p=0.015) (Table 2). The cell recovery using the AG-based cryopreservation solution was comparable to that observed when the cells were cryopreserved in 10 v/v % $Me_2SO$ solution in a mechanical freezer (p=0.941). These results indicate that the solutions can be used in mechanical and controlled-rate freezers.

TABLE 2

Cell recovery for PBLs from normal donors cryopreserved in a mechanical freezer at −80° C. using different solution compositions and effective cooling rates.

| Solution Composition | B[1] (° C./minute) | Cell recovery (%) |
|---|---|---|
| 3 v/v % glycerol + 15 w/v % AG + Normosol-R | 6 | 45 ± 2 (n = 3) |
| 3 v/v % glycerol + 15 w/v % AG + Normosol-R | 4 | 101 ± 24 (n = 3) |
| 10 v/v % $Me_2SO$ + IMDM | 1.4 | 100 ± 26 (n = 6) |

[1]Approximate cooling rate based on temperature recordings.

TABLE 3

Cell recovery for control cultures of PBLs or activated PBLs cryopreserved using two different protocols.

| Solution | B (° C./minute) | Activated Cells Cell Recovery (%) | Control cultured[1] Cell Recovery (%) |
|---|---|---|---|
| 15 w/v % AG + 3 v/v % glycerol + Normosol-R ™ | 5 | 74 ± 9 (n = 3) | 62 ± 1 (n = 3) |
| 10 v/v % $Me_2SO$ + IMDM | 1 | 101 ± 26 (n = 12) | 101 ± 33 (n = 12) |

[1]PBLs cultured without exogenous IL-2 for the same period of time as the activated cells.

TABLE 4

Overall recovery of frozen-thawed genetically modified PBLs from a donor with MPS II and freshly isolated cells from a normal donor.

| Solution | B (° C./minute) | Patients with MPS II Cell Recovery (%) | Normal Donors Cell Recovery (%) |
| --- | --- | --- | --- |
| 15 w/v % AG + 3 v/v % glycerol + IMDM | 5 | 62.2 ± 6.3 | 80.8 ± 15.7 |
| 10% DMSO | 1 | 51.7 ± 32.1 | 41 ± 3 |

Cryopreservation of Activated Lymphocytes

Figure 5:
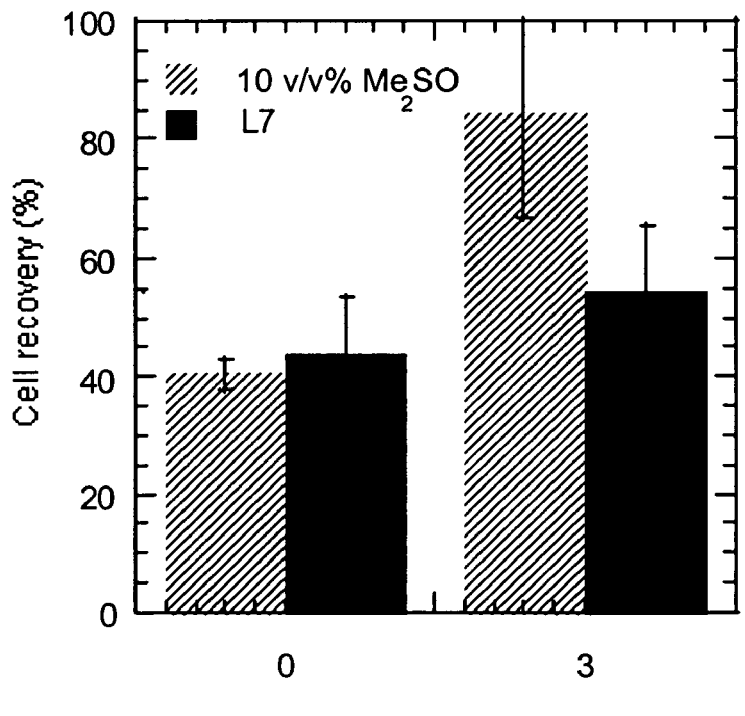
FIG. 5 illustrates percent cell recovery for PBLs from normal donors cryopreserved after 0 and 3 days in culture using (1) 10 v/v % $Me_2SO$, cooling rate (B)=1° C./minute, and (2) 3 v/v % glycerol+15 w/v % AG+Normosol-R™, B=5° C./minute. Error bars indicate the standard deviation of the measurement.

Immunotherapy protocols in development and clinical use may require short-term culture of the cells for activation or other modifications. To test the freezing response of the lymphocytes after short-term ex vivo culture, two different protocols were tested: (1) 10 v/v % Me$_2$SO+IMDM with a cooling rate of 1° C./minute; and (2) 15 w/v % AG+3 v/v % glycerol+Normosol-R™ with a cooling rate of 5° C./minute. Cells from the same donor were divided into two different aliquots. The cells from the first aliquot were cultured in the same media without the presence of exogenous IL-2. The second aliquot was activated using the protocol described previously. After 18 hours of ex vivo cultures, both samples were resuspended in the cryopreservation solution of interest and frozen. The cell recovery from these samples is summarized in Table 3. These results indicate that there is no statistically significant difference in the post-thaw viability of the cultured cells and activated cells. In contrast, if PBLs are cryopreserved freshly isolated or cultured for three days using the protocol described previously, the postthaw viability of the cells increases for both of the protocols evaluated (FIG. 5).

Cryopreservation of Genetically Modified PBLs

Recent studies suggest that ex vivo culture of hematopoietic cells influences their ability to withstand freeze-thaw stresses (Hubel, 1999). Genetically modified cells from donors with MPS II were cryopreserved using solutions described above with cells from normal donors. The overall recovery of genetically modified cells from a donor with MPS II was less than that observed for freshly isolated cells from a normal donor (Table 4). In order to determine if optimal freezing conditions are different for the genetically modified cells, additional samples were cryopreserved using cooling rates ranging between 1 and 10° C./minute. The postthaw cell recoveries observed using the range of cooling rates studied were no greater than that observed at 5° C./minute. Increasing the concentration of glycerol slightly to 5 v/v % increased postthaw cell recovery observed (77±43%).

EXAMPLE 2

Methods

Cells and Pre-Freeze Processing Techniques

All freezing studies were performed using umbilical cord blood obtained from normal donors with informed consent and approval from the local Institutional Review Board. In order to remove contaminating erythrocytes as well as autologous plasma from the sample to be frozen, the product was purified using a density gradient separation technique. Briefly, 5 ml of Histopaque (Sigma, St. Louis, Mo.) was added to a 15 ml conical tube. The product was diluted in a 1:5 ratio with phosphate buffered saline solution and layered over the Histopaque. The tubes containing the apheresis product and Histopaque were spun at 500 g for 30–45 minutes. The band of mononuclear cells at the liquid—liquid interface was removed and used for the subsequent freezing experiments after one step wash. The resulting mononuclear cells were resuspended in the cryopreservation solution of interest and placed in either a freezing vial (Cryovial, Nunc, Napierville, Ill.) or a bag (Cryo-Cyte, Baxter, Round Lake, Ill.) to a final cell concentration of approximately 30×10$^6$ cells/ml (range 20 to 50×10$^6$ cells/ml).

Cryopreservation Solution Reagents

The solutions tested contained IMDM supplemented with AG, human serum albumin and glycerol in various concentrations.

Thawing

After completion of the freezing process, all samples were removed from the controlled rate freezer and placed in a liquid nitrogen storage dewar (Model XLC-230, MVE, Bloomington, Minn.). At a time of no greater than 4 months with an average of approximately 2 weeks, the cells were removed from storage and thawed. The thawing of the sample was performed by placing the sample in a 37° C. water bath until all visible ice crystals had disappeared. The thawing protocol developed was designed to result in a rapid thawing of the sample intended to minimize recrystallization or osmotic injury experienced during the rewarming phase of the protocol.

Viability Assays

A variety of in vitro viability assays was performed in order to assess the viability and percentage recovery of stem cells. After completion of the thawing protocols, the frozen-thawed sample was mixed using a syringe to ensure even distribution of cells. Aliquots from the thawed sample were removed and used to determine (1) membrane integrity of the cells using fluorescent markers, Acridine Orange (AO) and Propidium Iodine (PI); (2) total cell counts using a hemocytometer; (3) proliferative capability of cells in a methylcellulose culture.

Briefly, in order to determine membrane integrity using AO/PI, 5 μl of cell suspension was diluted with 95 μl of IMDM. Equal amounts of cell suspension and AO/PI solution (Sigma, St. Louis, Mo.) were added and the sample was placed on the hemocytometer and counted using fluorescent microscopy (Zeiss Axioskop, Germany). Cells that fluoresced green were considered viable while those cells were red/orange were considered dead. By determining the total number of cells within a given region of the hemocytometer, it is possible to determine the cell concentration which when multiplied by the total volume results in the total cell number in the sample.

In order to determine proliferative capability of the cells, an aliquot of the sample was spun at 500 g for 2 minutes and the supernatant removed. The pellet was resuspended in IMDM to a final concentration of 2×10$^6$ viable cells/ml. Subsequently, 20,000 and 50,000 cells were added to 1 ml of MethoCult (Stem Cell Technologies, Vancouver, BC), methylcellulose culture medium for stem cells. The mixture was supplemented with IMDM+2% Fetal Calf Serum (Gibco, Grand Island, N.Y.), mixed and pipetted into 35×10 mm petri dishes (Falcon, Plymouth, England). The cultures were then placed in a misted air incubator for 2 weeks and colony formation was determined. Colonies were scored for CFU-GM, CFU-GEMM and BFU-E. The total number of colonies was also counted. For ease of data representation, the total colony numbers for a given seeding density was determined. A similar set of colony assays was performed on the pre-freeze sample as a direct control. The percentage colony recovery was determined by dividing the total number of colonies counted post freeze-thaw by that obtained in the prefreeze product for the same cell seeding density. These assays permitted the determination of the total viable cell yield (total viable number of cells post freeze-thaw divided by the total number of viable cells pre freeze-thaw), the cells expressing membrane integrity and the proliferative capability of the cells.

Results

The results shown in Table 5 indicate that hematopoietic progenitor cells can be effectively cryopreserved in solutions containing AG.

TABLE 5

| Solution[1] | B (C./min) | % MNCs viable | % Colony Recovery[1] |
|---|---|---|---|
| 15% AG + 1% v/v HSA | 10 | 76 | 24 ± 1 |
| 15% AG + 1% v/v glycerol + 1% v/v HSA | 5 | 88 ± 1 | 111 ± 28 |

[1]base of a solution is tissue culture medium, IMDM.
[2]total number of colonies posthaw divided by the total number of colonies obtained from a fresh sample from the same donor. The seeding density for the colonies is 50,000.

REFERENCES

Abe et al., *J. Virol.*, 72:6159 (1998)
Areman et al., *Bone Marrow Transplant*, 6, 203 (1990).
Areman et al., *Transfusion*, 28, 151 (1988). *Bone Marrow and Stem Cell Processing: A Manual of Current Techniques*, edited by Areman et al., F. A. Davis Company (1992).
Blaese et al., *Science*, 270, 475 (1995).
Bonini et al., *Science*, 216, 1719 (1997).
Branden et al., *Nat. Biotech.*, 17, 784 (1999).
Champlin, *J. Hematotherapy*, 4, 53–60 (1995).
Davis et al., *Blood*, 75, 781 (1990).
Fahy et al., *Cryobiology*, 27, 247–268 (1990).
Fraser et al., *J. Hematother.*, 7, 521 (1998).
Hubel, *Cryobiology*, 38, 140 (1999).
Kawakami et al., *J. Immunother.*, 21, 237 (1998).
Koenig et al., *Nature Medicine*, 1, 330 (1995).
Kolb et al., *Current Opin. Oncol.*, 9, 139 (1997).
Mochizuki et al., *J. Virol.*, 72, 8873 (1998).
Nei, *Cryobiology*, 18, 229 (1981).
Noga, *J. Hematotherapy*, 1, 3 (1992).
Okamoto et al., *Transfusion*, 31, 578 (1991).
Pan, Ph. D. Thesis, University of Minnesota (1997).
Pegg, *Cryobiology*, 9, 411 (1972).
Preti et al., *J. Hematotherapy*, 2, 103 (1993).
Rosenberg et al., *N. Engl. J. Med.*, 316, 889 (1987a).
Rosenberg et al., *N. Engl. J. Med.*, 319, 1676 (1987b).
Rosenberg et al., *N. Engl. J. Med.*, 313, 1485 (1985).
Rowley et al., *Blood*, 83, 2731 (1994).
Rowley, *J. Hematotherapy*, 1,233. (1992)
Shankar et al., *Transfusion*, 37, 685 (1997).
Stroncek et al., *Transfusion*, 39, 343 (1999a).
Stroncek et al., *Transfusion*, 31, 521 (1991).
Torpey et al., *Clin. Immunol. and Immunopath.*, 68, 263 (1993).
Trickett et al., *J. AIDS and Hum. Retro.*, 17, 129 (1998).
Verfaillie et al., *J. Exp. Med.*, 172, 509 (1990).
Zambelli et al., *Anticancer Res.*, 18, 4705 (1998).

It is understood that the above description is intended to be illustrative, not restrictive. Other embodiments will be apparent to those of skill in the art, given the disclosure provided herein by the inventors. The scope of the invention should, therefore, be determined with reference to the appended claims, along with the full scope of equivalents to which such claims are entitled.

All referenced publications, patents and patent documents are intended to be incorporated by reference, as though individually incorporated by reference.

What is claimed is:

1. A cryopreservation medium comprising a balanced electrolyte solution, a cryoprotective agent that is arabinogalactan, or a biological or functional equivalent thereof, in an amount of 1% w/v to 40% w/v, a cryoprotective agent that penetrates the cell membrane, and freshly isolated lymphocytes, hematopoietic stem cells, lymphocytes which are modified ex vivo, or a combination thereof, wherein the medium does not comprise dimethylsulfoxide or serum, and wherein the arabinogalactan, a biological or functional equivalent thereof, in the medium results in a high post-thaw survival rate for the freshly isolated lymphocytes, hematopoietic stem cells, or lymphocytes which are modified ex vivo.

2. The cryopreservation medium of claim 1 wherein the cells are peripheral blood lymphocytes.

3. The cryopreservation medium of claim 1 that comprises arabinogalactan.

4. The cryopreservation medium of claim 1 wherein the cryoprotective agent that penetrates the cell membrane is glycerol or propylene glycol.

5. The cryopreservation medium of claim 1 further comprising a cryoprotective agent other than arabinogalactan or a biological or functional equivalent thereof which does not penetrate the cell membrane.

6. The cryopreservation medium of claim 1 which does not comprise protein.

7. The cryopreservation medium of claim 1 which is infusible.

8. The cryopreservation medium of claim 1 wherein the cells are human cells.

9. The cryopreservation medium of claim 1 wherein the cells are non-human vertebrate cells.

10. A composition suitable for administration to a human, comprising a suspension of cells in a cryopreservation medium comprising a balanced electrolyte solution, a cryoprotective agent that is arabinogalactan, or a biological or functional equivalent thereof, in an amount of 1% w/v to 40% w/v, and a cryoprotective agent that penetrates the cell membrane, wherein the cells are freshly isolated lymphocytes, hematopoietic stem cells, lymphocytes which are modified ex vivo, or a combination thereof, and wherein the medium does not comprise dimethylsulfoxide or serum.

11. The composition of claim 10 wherein the cells are peripheral blood lymphocytes.

12. The composition of claim 10 wherein the medium comprises arabinogalactan.

13. The composition of claim 10 wherein the cryoprotective agent that penetrates the cell membrane is glycerol or propylene glycol.

14. The composition of claim 10 further comprising a cryoprotective agent other than arabinogalactan or a biological or functional equivalent thereof which does not penetrate the cell membrane.

15. The composition of claim 10 which does not comprise protein.

16. The composition of claim 10 which is infusible.

17. The composition of claim 10 wherein the cells are human cells.

18. A method for preserving cells comprising:
(a) contacting cells with a cryopreservation medium comprising a balanced electrolyte solution, a cryoprotective agent that is arabinogalactan, or a biological or functional equivalent thereof, in an amount of 1% w/v to 40% w/v, and a cryoprotective agent that penetrates the cell membrane, to yield a cell suspension, wherein the cells are freshly isolated lymphocytes, hematopoietic stem cells, lymphocytes which are modified ex vivo, or a combination thereof, wherein the medium does not comprise dimethylsulfoxide or serum, and wherein the arabinogalactan, a biological or functional equivalent thereof, in the medium results in a high post-thaw survival rate for the freshly isolated lymphocytes, hematopoietic stem cells, or lymphocytes which are modified ex vivo; and
(b) freezing the cell suspension to yield a frozen cell suspension.

19. The method of claim 18 further comprising thawing the frozen cell suspension under conditions that maintain cell viability.

20. The method of claim 18 wherein the cells are human cells.

21. The method of claim 18 wherein the cells are peripheral blood lymphocytes.

22. A frozen composition comprising i) inorganic salts capable of maintaining physiological pH when in solution, ii) a cryoprotective agent that is arabinogalactan, or a biological or functional equivalent thereof, in an amount of 1% w/v to 40% w/v, iii) a cryoprotective agent that penetrates the cell membrane, and iv) freshly isolated lymphocytes, hematopoietic stem cells, lymphocytes which are modified ex vivo, or a combination thereof, wherein the composition does not comprise dimethylsulfoxide or serum.

23. A frozen hematopoietic cell-containing composition made according to the method of claim 18.

24. The cryopreservation medium of claim 4 wherein the cryoprotective agent that penetrates the cell membrane is glycerol.

25. The cryopreservation medium of claim 24 wherein the concentration of glycerol is about 1% to about 3%.

26. The cryopreservation medium of claim 1 wherein the lymphocytes which are modified ex vivo are activated lymphocytes or genetically modified lymphocytes.

27. The composition of claim 10 or 22 wherein the lymphocytes which are modified ex vivo are activated lymphocytes or genetically modified lymphocytes.

28. A cryopreservation medium comprising a balanced electrolyte solution, at least one cryoprotective agent that is arabinogalactan, or a biological or functional equivalent thereof, in an amount of 1% w/v to 40% w/v and freshly isolated lymphocytes, hematopoietic stem cells, lymphocytes which are modified ex vivo, or a combination thereof, wherein the medium does not comprise dimethylsulfoxide or serum, and wherein the balanced electrolyte solution is selected from the group consisting of lactated Ringer's solution, PlasmaLyte-A™, Normosol-R™, Veen-D™, Polysal®, and Hank's balanced salt solution.

29. The cryopreservation medium of claim 28 wherein the lymphocytes are peripheral blood lymphocytes.

30. The cryopreservation medium of claim 28 wherein the agent is arabinogalactan.

31. The cryopreservation medium of claim 28 further comprising a cryoprotective agent that penetrates the cell membrane.

32. The cryopreservation medium of claim 31 wherein the cryoprotective agent that penetrates the cell membrane is glycerol or propylene glycol.

33. The cryopreservation medium of claim 28 further comprising a cryoprotective agent other than arabinogalactan or a biological or functional equivalent thereof which does not penetrate the cell membrane.

34. The cryopreservation medium of claim 28 which does not comprise protein.

35. The cryopreservation medium of claim 28 which is infusible.

36. The cryopreservation medium of claim 28 wherein the cells are human cells.

37. The cryopreservation medium of claim 28 wherein the cells are non-human vertebrate cells.

38. The method of claim 18 wherein the medium comprises arabinogalactan.

39. A cryopreservation medium comprising a balanced electrolyte solution, a cryoprotective agent that is arabinogalactan, in an amount of 1% w/v to 40% w/v, a cryoprotective agent that penetrates the cell membrane, and freshly isolated lymphocytes, hematopoietic stem cells, lymphocytes which are modified ex vivo, or a combination thereof, wherein the medium does not comprise dimethylsulfoxide or serum, and wherein the arabinogalactan in the medium results in a high post-thaw survival rate for the freshly isolated lymphocytes, hematopoietic stem cells, or lymphocytes which are modified ex vivo.

40. A cryopreservation medium comprising a balanced electrolyte solution, a cryoprotective agent that is arabinogalactan, which is present in an amount of 1% w/v to 40% w/v, glycerol in amount of 0.5% to about 20%, and freshly isolated lymphocytes, hematopoietic stem cells, lymphocytes which are modified ex vivo, or a combination thereof, wherein the medium does not comprise dimethylsulfoxide or serum, and wherein the arabinogalactan in the medium results in a high post-thaw survival rate for the freshly isolated lymphocytes, hematopoietic stem cells, or lymphocytes which are modified ex vivo.

41. A frozen composition comprising i) inorganic salts capable of maintaining physiological pH when in solution, ii) a cryoprotective agent that is arabinogalactan in an amount of 1% w/v to 40% w/v, iii) a cryoprotective agent that penetrates the cell membrane, and iv) freshly isolated lymphocytes, hematopoietic stem cells, lymphocytes which are modified ex vivo, or a combination thereof, wherein the composition does not comprise dimethylsulfoxide or serum, and wherein the arabinogalactan in the composition results in a high post-thaw survival rate for the freshly isolated lymphocytes, hematopoietic stem cells, or lymphocytes which are modified ex vivo.

42. A frozen composition comprising i) inorganic salts capable of maintaining physiological pH when in solution, ii) a cryoprotective agent that is arabinogalactan in an amount of 1% w/v to 40% w/v, iii) glycerol in amount of 0.5% to about 20%, and iv) freshly isolated lymphocytes, hematopoietic stem cells, lymphocytes which are modified ex vivo, or a combination thereof, wherein the composition does not comprise dimethylsulfoxide or serum, and wherein the arabinogalactan in the composition results in a high post-thaw survival rate for the freshly isolated lymphocytes, hematopoietic stem cells, or lymphocytes which are modified ex vivo.

43. A method for preserving cells comprising: freezing a cell suspension comprising cells and a cryopreservation medium comprising a balanced electrolyte solution, arabinogalactan in an amount of 1% w/v to 40% w/v, and glycerol in amount of 0.5% to about 20%, wherein the cells are freshly isolated lymphocytes, hematopoietic stem cells, lymphocytes which are modified ex vivo, or a combination thereof, wherein the medium does not comprise dimethylsulfoxide or serum, and wherein the arabinogalactan in the medium results in a high post-thaw survival rate for the freshly isolated lymphocytes, hematopoietic stem cells, or lymphocytes which are modified ex vivo.

44. A method for preserving cells comprising:
(a) contacting cells with a cryopreservation medium comprising a balanced electrolyte solution, a cryoprotective agent that is arabinogalactan, in an amount of 1% w/v to 40% w/v, and a cryoprotective agent that penetrates the cell membrane, to yield a cell suspension, wherein the cells are freshly isolated lymphocytes, hematopoietic stem cells, lymphocytes which are modified ex vivo, or a combination thereof, and wherein the medium does not comprise dimethylsulfoxide or serum; and
(b) freezing the cell suspension at a cooling rate of about 1° to about 10° C./minute to yield a frozen cell suspension.

45. The medium of claim 1, 28, 39 or 40 wherein the post-thaw survival rate is at least about 40%.

46. The method of claim 18, 43 or 44 wherein the post-thaw survival rate is at least about 40%.

47. A cryopreservation medium comprising a balanced electrolyte solution, arabinogalactan, or a biological or functional equivalent thereof, in an amount of 1% w/v to 40% w/v, and a cryoprotective agent that penetrates the cell membrane.

48. The medium of claim 47 wherein the cryoprotective agent that penetrates the cell membrane is glycerol or propylene glycerol.

49. The medium of claim 48 wherein glycerol is about 1% to about 5%.

50. The cryopreservation medium of claim 47 wherein the arabinogalactan is about 10% w/v to about 30% w/v.

51. The method of claim 18, 43 or 44 wherein the cryoprotective agent that penetrates the cell membrane is glycerol or propylene glycol.

52. The method of claim 18, 43 or 44 wherein the lymphocytes which are modified ex vivo are activated lymphocytes or genetically modified lymphocytes.

* * * * *

UNITED STATES PATENT AND TRADEMARK OFFICE
CERTIFICATE OF CORRECTION

PATENT NO. : 7,112,576 B1
APPLICATION NO. : 09/458862
DATED : September 26, 2006
INVENTOR(S) : Allison Hubel It is certified that error appears in the above-identified patent and that said Letters Patent is hereby corrected as shown below:

On the face page, in field (56), under "Other Publications", in column 2, line 2, delete "Millenium?" and insert -- Millennium? --, therefor.

On the face page, in field (56), under "Other Publications", in column 2, line 18, delete "Rabit" and insert -- Rabbit --, therefor.

On the face page, in field (56), under "Other Publications", in column 2, line 20, delete "Stroneck," and insert -- Stroncek, --, therefor.

On the face page, in field (56), under "Other Publications", in column 2, line 34, delete "Cyropreservation"," and insert -- Cryopreservation", --, therefor.

On the face page, in field (56), under "Other Publications", in column 2, line 48, delete "Eletroylyte" and insert -- Electrolyte --, therefor.

On page 2, in field (56), under "Other Publications", in column 1, line 13, delete "Hematotheraphy," and insert -- Hematotherapy, --, therefor.

On page 2, in field (56), under "Other Publications", in column 1, line 24, delete "chemo-radiotheraphy" and insert -- chemo-radiotherapy --, therefor.

On page 2, in field (56), under "Other Publications", in column 1, line 36, after "donor"" insert -- , --.

On page 2, in field (56), under "Other Publications", in column 1, line 37, delete "Granuloucyte" and insert -- Granulocyte --, therefor.

On page 2, in field (56), under "Other Publications", in column 1, line 47, delete "CD34+Results"," and insert -- CD34+ Results", --, therefor.

On page 2, in field (56), under "Other Publications", in column 1, line 48, delete "Infusionether" and insert -- Infusionsther --, therefor.

On page 2, in field (56), under "Other Publications", in column 1, line 52, delete "Hermat.," and insert -- Hemat., --, therefor.

On page 2, in field (56), under "Other Publications", in column 1, line 54, delete "Haemopoietic" and insert -- Hematopoietic --, therefor.

On page 2, in field (56), under "Other Publications", in column 2, line 12, delete "degree" and insert -- Degree --, therefor.

UNITED STATES PATENT AND TRADEMARK OFFICE
CERTIFICATE OF CORRECTION

PATENT NO.        : 7,112,576 B1
APPLICATION NO.   : 09/458862
DATED             : September 26, 2006
INVENTOR(S)       : Allison Hubel It is certified that error appears in the above-identified patent and that said Letters Patent is hereby corrected as shown below:

On page 2, in field (56), under "Other Publications", in column 2, line 17, delete "Hematotheraphy," and insert -- Hematotherapy, --, therefor.

On page 2, in field (56), under "Other Publications", in column 2, line 27, delete "haemopoietic" and insert -- hematopoietic --, therefor.

On page 2, in field (56), under "Other Publications", in column 2, line 28, delete "bolld," and insert -- blood, --, therefor.

On page 2, in field (56), under "Other Publications", in column 2, line 31, delete "Socierty" and insert -- Society --, therefor.

On page 2, in field (56), under "Other Publications", in column 2, line 37, delete "Haemopoietic" and insert -- Hematopoietic --, therefor.

On page 2, in field (56), under "Other Publications", in column 2, line 54, delete "CD34+Cell" and insert -- CD34+ Cell --, therefor.

On page 2, in field (56), under "Other Publications", in column 2, line 59, delete "Clony" and insert -- Colony --, therefor.

On page 2, in field (56), under "Other Publications", in column 2, line 63, delete "degree" and insert -- Degree --, therefor.

On page 2, in field (56), under "Other Publications", in column 2, line 64, delete "Hermatology," and insert -- Hematology, --, therefor.

Figure 4:
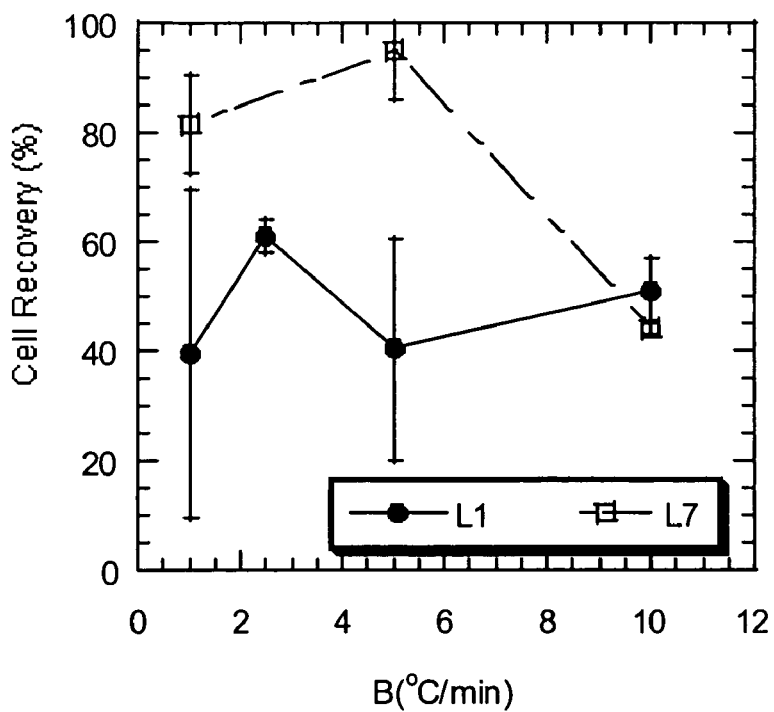
FIG. 4 shows percent recovery for PBLs from normal donors cryopreserved in solutions containing 15 w/v % AG+x v/v % glycerol+IMDM as a function of cooling rate. Error bars indicate the standard deviation of the measurement.

On sheet 3 of 3, in fig. 4, line 1, delete "B(°C/min)" and insert -- B(°C./min) --, therefor.

In column 1, line 36, delete "melanomal" and insert -- melanoma --, therefor.

In column 5, line 58, delete "methycellulose." and insert -- methylcellulose. --, therefor.

In column 11, line 36, delete "hydoxyethyl" and insert -- hydroxyethyl --, therefor.

In column 16, line 48, delete "(DNAse," and insert -- (DNase, --, therefor.

In column 20, line 63, delete "R $^{TM}$" and insert -- R$^{TM}$ --, therefor.

In column 23, line 27, delete "posthaw" and insert -- postthaw --, therefor.

UNITED STATES PATENT AND TRADEMARK OFFICE
CERTIFICATE OF CORRECTION

PATENT NO.        : 7,112,576 B1
APPLICATION NO.   : 09/458862
DATED             : September 26, 2006
INVENTOR(S)       : Allison Hubel It is certified that error appears in the above-identified patent and that said Letters Patent is hereby corrected as shown below:

In column 23, line 33, after "(1998)" insert -- , --.

In column 23, line 40, delete "216," and insert -- 276, --, therefor.

In column 23, line 62, delete "1,233. (1992)" and insert -- 1, 233 (1992). --, therefor.

In column 25, line 2, in Claim 14, after "arabinogalactan" delete "or a".

In column 25, line 3, in Claim 14, after "thereof" insert -- , --.

In column 25, line 62, in Claim 28, after "are" insert -- activated or genetically --.

In column 25, line 64, in Claim 28, after "serum," delete "and".

In column 25, line 67, in Claim 28, after "solution" delete "." and insert -- and wherein the arabinogalactan, biological or functional equivalent thereof, results in a high post-thaw survival rate for the freshly isolated lymphocytes, hematopoietic stem cells, or lymphocytes which are activated or genetically modified ex vivo. --, therefor.

Signed and Sealed this

Sixteenth Day of October, 2007

JON W. DUDAS
*Director of the United States Patent and Trademark Office*